United States Patent [19]

Fair et al.

[11] Patent Number: 5,190,919
[45] Date of Patent: Mar. 2, 1993

[54] ANTIHEMOSTATIC FACTOR VII PEPTIDES

[75] Inventors: Daryl S. Fair; Anuradha Kumar, both of Tyler, Tex.

[73] Assignee: Board of Regents, The University of Texas System, Austin, Tex.

[21] Appl. No.: 435,657

[22] Filed: Nov. 13, 1989

[51] Int. Cl.$^5$ .................. A61K 37/00; A61K 37/02; C07K 5/00; C07K 7/00
[52] U.S. Cl. .......................... 514/15; 514/12; 514/13; 514/14; 530/328; 530/327; 530/326; 530/325; 530/324
[58] Field of Search ................ 514/12, 13, 14, 15, 514/16, 17; 530/324, 326, 327, 328, 329

[56] References Cited

U.S. PATENT DOCUMENTS

| | | | |
|---|---|---|---|
| 4,736,018 | 4/1988 | Reutelingsperger | 530/381 |
| 4,772,686 | 9/1988 | Szelke et al. | 530/331 |
| 4,791,100 | 12/1988 | Kramer et al. | 514/12 |

OTHER PUBLICATIONS

Hagen et al., Proc. Natl. Acad. Sci. USA, vol. 83, pp. 2412-2416 (1986).
Ohara et al., Proc. Natl. Acad Sci. USA, vol. 84, pp. 5158-5162 (1987).
Thim et al., Biochemistry, 27, pp. 7785-7793, 1988.

*Primary Examiner*—Merrell C. Cashion, Jr.
*Assistant Examiner*—A. M. Davenport
*Attorney, Agent, or Firm*—Arnold, White & Durkee

[57] ABSTRACT

A number of novel antihemostatic peptides are claimed. Included among the antihemostatic peptides claimed are R-T-K-L-F-W-I-S-Y-S-D-G-D-Q, Y-S-D-G-D-Q-C, L-L-V-N-G-A-Q-L-C, C-F-D-K-I-K-N-W-R-N-L-I-A-V-L-G-E-H-D-L-S, F-D-K-I-K-N-W-R-N-L-I-A-V-L-G-E-H-D-L-S-E-H-D-G-D-E-Q-S-R-R-V-A-Q-V-I, L-G-E-H-D-L-S-E-H-D-G-D-E-Q-S-R-R-V-A-Q-V-I, A-V-L-G-E-H-D-L-S-E-H-D-G, V-R-F-S-L-V-S-G-W-G-Q, G-Q-L-L-D-R-G-A-T-A-L-E-L-M-V-L-N-V-P-R-L, A-G-Y-S-D-G-S-K-D-S-C, P-H-A-T-H-Y-R-G-T-W-Y-L-T-G-I and V-Y-T-R-V-S-Q-Y-I-E-W-L-Q-K-L and their analogues. The peptides are useful for inhibiting the formation of the Factor VII-tissue factor macromolecular complex of for inhibiting the activation of Factor X by Factor VII.

8 Claims, 17 Drawing Sheets

<br>

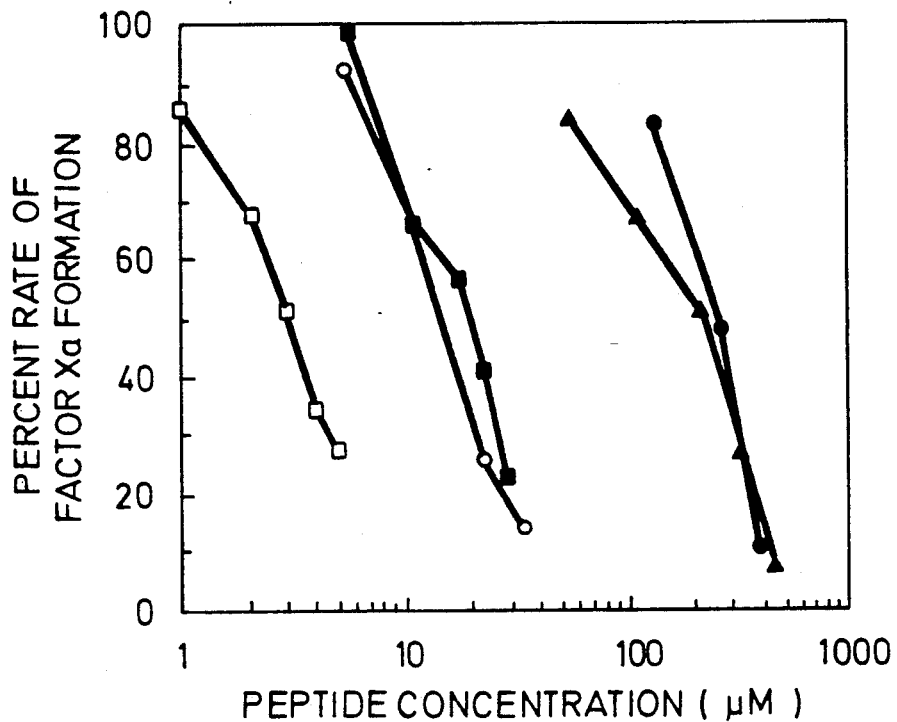
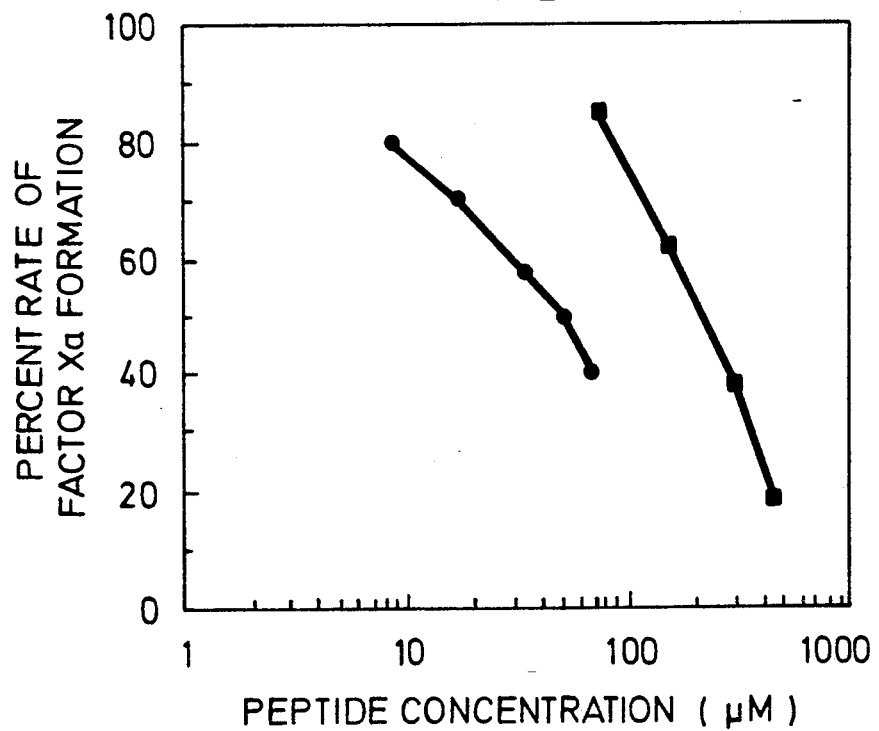

ANTIHEMOSTATIC FACTOR VII PEPTIDES

The development of this invention was aided by a research grant HL 37770 of the National Institutes of Health. Accordingly, the government may own certain rights.

FIELD OF THE INVENTION

The present invention relates to novel peptide reagents, useful as pharmaceutical agents for preventing blood clot formation. The invention also includes pharmaceutical compositions comprising such compounds. The specification of Applicant's copending application, Ser. No. 371,561 is incorporated herein by reference.

BACKGROUND OF THE INVENTION AND DESCRIPTION OF RELATED ART

Anticoagulants are used in the treatment of a wide variety of thrombotic disorders and in the laboratory to prevent the clotting of conserved blood. Heparin, for example, is widely used against thrombosis, but administration of heparin carries a high risk of hemorrhage or thrombocytopenia; is ineffective in many conditions, and may produce unpredictable results including recurrent thromboembolism. Derivatives of 4-hydroxycoumarin or of 1,4 idanedione also have a number of disadvantages. It is difficult to maintain a therapeutic dose due to a wide variability in the patient's diet, effective drug dose, and drug metabolism. Hemorrhage is a common complication and treatment of this side effect which may require the use of potentially hazardous (virus containing) plasma.

Other anticoagulants include those endogenous to the plasma, for example, antithrombin III, the extrinsic pathway inhibitor, and proteins obtained from certain plants and organisms, including the leech-derived polypeptides provided by U.S. Pat. No. 4,971,100 and Kunitz inhibitor obtained from soybean. The latter blocks the blood coagulation cascade by inhibition of activated Factor X, but the specificity of the inhibitor is so low that many side effects develop, including for example, inhibition of plasma kallikrein, plasmin and trypsin. Other active compounds, such as the Ascaris or Kazals inhibitor have also been criticized for their lack of specificity.

The complexity of the blood coagulation system exacerbates the need for an acceptable pharmaceutical agent capable of inhibiting hemostasis at a specifically defined point in the pathway. Clotting results from a complex series of interactions, which culminate in the thrombin-mediated cleavage of fibrinogen to fibrin and its subsequent crosslinking (1). Thrombin production may result from either of two pathways, an "intrinsic" pathway based on circulating blood components and an "extrinsic" pathway requiring a tissue-derived component. In each system, there is a cascade of reactions during which each of a series of inactive factors is converted by a proteolytic reaction into the corresponding active or "a" factor that is itself a proteolytically active enzyme or a non-proteolytically active cofactor capable of effecting the next step in the reaction cascade.

In the intrinsic activation pathway, circulating Factor XII (Hageman Factor) is postulated to bind to negatively charged surfaces or damaged aggregated platelets. Kallikrein cleaves Factor XII to form Factor XIIa. Factor XIIa, in the presence of high molecular weight kininogen, 1) cleaves circulating Factor XI (plasma thromboplastin antecedent) to Factor XIa (plasma thromboplastin) and 2) cleaves circulating prekallikrein to active kallikrein, effecting amplification of the pathway. Factor XIa, in the presence of calcium ions, cleaves circulating Factor IX (Christmas Factor) to Factor IXa Factor IXa, with circulating Factor VIII (antihemophilic globulin or AHG) in the presence of calcium ions and cell-derived phospholipid, forms a lipoprotein complex with circulating Factor X and cleaves it to form Factor Xa. Thus, in the intrinsic system, activation of Factor X requires the interaction of Factor IXa (enzyme) and Factor VIIIa (nonproteolytic cofactor) on a phospholipid surface in the presence of calcium ion.

In the extrinsic activation pathway, Factor VII associates with an integral tissue lipoprotein called tissue thromboplastin or tissue factor (Factor III) and in the presence of calcium ions, forms a complex with circulating Factor X and cleaves it to form a second source of Factor Xa (2). Factor Xa cleaves tissue factor-bound Factor VII to Factor VIIa, a much more active enzyme, thus amplifying the effects of this pathway. Factor IX may also be converted to Factor IXa by Factor VIIa and tissue factor further amplifying Factor X activation through the "intrinsic" activation pathway. Thus, the extrinsic Factor X activation complex is composed of Factor VII/VIIa (enzyme) assembled with the integral membrane-bound non-proteolytic cofactor, tissue factor, in the presence of calcium ions. The extrinsic pathway of activation is probably the physiologically relevant system, as patients deficient in Factor XII, prekallikrein or high molecular weight kininogen do not have bleeding disorders. Deficiencies in the other blood coagulation components may all lead to hemophilia.

Factor X is activated by either the intrinsic or extrinsic activation pathways. Factor Xa, with activated Factor V and in the presence of calcium ions and cellular phospholipid, forms a lipoprotein complex with Factor II (prothrombin) and cleaves it to form thrombin (Factor IIa). In other words, Factor Xa (enzyme) associates with Factor Va (nonproteolytic cofactor) in a macromolecular membrane complex responsible for the activation of prothrombin.

Thrombin converts circulating fibrinogen to the insoluble form fibrin, which spontaneously polymerizes into filaments and is then crosslinked under the action of Factor XIIIa, an enzyme formed from Factor XIII by thrombin activation.

There is a considerable body of evidence that tissue factor is the major initiator of coagulation. Following injury to a vessel, the contact of blood with tissue factor may be a primary event in the hemostatic and thrombotic processes. Indeed, recent studies suggest that tissue factor activation of the extrinsic pathway of coagulation is the primary early event mediating the formation of fibrin and the arrest of bleeding (3,4).

As indicated above, because of the complexity of the blood coagulation system, the preferred anticoagulant is one that can be definitively targeted to a precise and specific early stage in the blood coagulation cascade. However, as stated above, in the past, such agents were not available or suffered from serious drawbacks, such as their toxicity or antigenicity in humans.

SUMMARY OF THE INVENTION

Therefore, the present inventors have now discovered a number of novel antihemostatic Factor VII peptides which can be specifically targeted to the extrinsic pathway by inhibiting either the initial step of coagulation (the formation of the Factor VII-tissue factor complex) or the activation of Factor X and which overcome the disadvantages of the type set forth above.

In its most general sense, the invention comprises antihemostatic peptides capable of inhibiting the extrinsic pathway of blood coagulation by preventing the rate of association of Factor VII with tissue factor or by inhibiting the rate of activation of Factor X by the assembled Factor VII-tissue factor macromolecular complex by at least about 40%. The invention also includes a number of antihemostatic peptides which inhibit Factor Xa by at least 40%. Preferably the test conditions will be similar to those set forth in the Examples, and more preferably to those set forth in Table 1. Using those conditions, one of ordinary skill-in-the-art can determine percent of inhibition as described herein.

One preferred embodiment of the invention comprises a peptide of about 6-15 amino acids that contains a sequence of amino acids that is at least 90% homologous to a peptide sequence R-T-K-L-F-W-I-S-Y-S-D-G-D-Q-C. The invention also comprises the peptide sequence: R-T-K-Q-F-W-I-S-Y-S-D-G-D-Q-C, where glutamine is substituted for leucine. In another preferred embodiment, the peptide will comprise about 8–15 amino acids which contain a stretch of amino acids exhibiting at least 95% homology to the following peptide: L-L-V-N-G-A-Q-L-C. A third preferred embodiment comprises a peptide of about 12–36 amino acids exhibiting at least 95% homology to the amino acid sequence: C-F-D-K-I-K-N-W-R-N-L-I-A-V-L-G-E-H-D-L-S-E-H-D-G-D-E-Q-S-R-R-V-A-Q-V-I. Even more preferred is a peptide of about 12–21 amino acids exhibiting at least 95% homology to the amino acid sequence: C-F-D-K-I-K-N-W-R-N-L-I-A-V-L-G-E-H-D-L-S. A fifth preferred embodiment comprises a peptide of about 15–24 amino acids exhibiting at least 95% homology to the amino acid sequence: L-G-E-H-D-L-S-E-H-D-G-D-E-Q-S-R-R-V-A-Q-V-I-G-C. A sixth preferred embodiment comprises a peptide having about 11 amino acids exhibiting at least 95% homology to the amino acid sequence: V-R-F-S-L-V-S-G-W-G-Q. A. seventh preferred peptide comprises about 14–23 amino acids exhibiting at least 95% homology to a peptide sequence that is G-Q-L-L-D-R-G-A-T-A-L-E-L-M-V-L-N-V-P-R-L-G-C. In an eighth embodiment, the invention comprises an amino acid sequence of about 10–15 amino acids which exhibits at least 95% homology to a peptide sequence: A-G-Y-S-D-G-S-K-D-S-C. A ninth preferred peptide comprises about 14–17 amino acids and contains a stretch of amino acids exhibiting at least 95% homology to the peptide sequence: P-H-A-T-H-Y-R-G-T-W-Y-L-T-G-I-G-C. In a tenth embodiment, the preferred peptide comprises about 15 amino acids which exhibit at least 95% homology to the peptide sequence: V-Y-T-R-V-S-Q-Y-I-E-W-L-Q-K-L.

For the purposes of the present invention, amino acid homology may be determined by methods known to those of skill-in-the-art, for example, by the method utilized by McLacklin (5).

The invention also comprises a number of peptides having specific amino acid sequences. These sequences include: Y-S-D-G-D-Q-C, R-T-K-L-F-W-I-S-Y-S-D-G-D-Q, L-L-V-N-G-A-Q-L-C, C-F-D-K-I-K-N-W-R-N-L-I-A-V-L-G-E-H-D-L-S, F-D-K-I-K-N-W-R-N-L-I-A-V-L-G-E-H-D-L-S-E-H-D-G-D-E-Q-S-R-R-V-A-Q-V-I, L-G-E-H-D-L-S-E-H-D-G-D-E-Q-S-R-R-V-A-Q-V-I, A-V-L-G-E-H-D-L-S-E-H-D-G, G-Q-L-L-D-R-G-A-T-A-L-E-L-M-V-L-N-V-P-R-L, A-G-Y-S-D-G-S-K-D-S-C, P-H-A-T-H-Y-R-G-T-W-Y-L-T-G-I, V-Y-T-R-V-S-Q-Y-I-E-W-L-Q-K-L, and V-R-F-S-L-V-S-G-W-G-Q.

Each peptide of the present invention will generally include less than about 100 amino acids, preferably from about 6 to 50 amino acids, and most preferably from about 6 to 36 amino acids. The peptides may be prepared using any of a number of methods known to those of skill-in-the art. Synthetic peptides synthesis is preferred as such synthesis automatically yields a substantially purified preparation of peptide which may be incorporated into pharmaceutical preparations and other compositions for the use in treatment of individuals without the need for the extensive purification procedures that would be required to separate the peptide from a complex protein mixture such as plasma. Once the peptides of the present invention have been prepared, they may be formulated into pharmaceutical preparations for the treatment of clotting or thrombotic disorders and other conditions where anticoagulant therapy is warranted, e.g., deep vein thrombosis, pulmonary embolism, arterial thrombotic disorders including acute arterial occlusion and disseminated intravascular coagulation.

The peptides may be administered directly or formulated together with any acceptable pharmaceutical excipient, including, for example, water, oil, water and oil emulsions, peptide in oil suspensions and any other suitable pharmaceutical formulations known to those of skill-in-the-art. In a preferred embodiment, the peptide will comprise at least 0.05% to 5% of the formulation by weight per unit volume.

Also included within the range of the invention is a method comprising the inhibition of the product of the Factor VII-tissue factor complex by inhibiting activated Factor X in individuals by administering to these individuals the peptide, P-H-A-T-H-Y-R-G-T-W-Y-L-T-G-I, together with a pharmaceutically acceptable excipient.

This invention also provides several methods for preventing 18 the formation of a Factor VII-tissue factor complex which initiates coagulation at a wound site in an individual. The most preferred method comprises administering to an individual the peptide, G-Q-L-L-D-R-G-A-T-A-L-E-L-M-V-L-N-V-P-R-L, together with a pharmaceutically acceptable excipient. Another preferred method for preventing Factor VII-tissue factor complex formation in an individual comprises administering a peptide selected from the group consisting of: a) Y-S-D-G-D-Q-C; or b) C-F-D-K-I-K-N-W-R-N-L-I-A-V-L-G-E-H-D-L-S; or c) L-G-E-H-D-L-S-E-H-D-G-D-E-Q-S-R-R-V-A-Q-V-I; or d) V-Y-T-R-V-S-Q-Y-I-E-W-L-Q-K-L; or e) V-R-F-S-L-V-S-G-W-G-Q together with a pharmaceutically acceptable excipient. A third method for prevention of a Factor VII-tissue factor complex formation in an individual comprises administering to said individual a peptide selected from the group consisting of : a) L-L-V-N-G-A-Q-L-C; or b) A-G-Y-S-D-G-S-K-D-S-C together with a pharmaceutically acceptable excipient.

This invention offers several methods for treating individuals with thrombotic disorders. A most preferred method for treating an individual with a thrombotic disorder(s) comprises administering to an individual the peptide, G-Q-L-L-D-R-G-A-T-A-L-E-L-M-V-L-N-V-P-R-L, together with a pharmaceutically acceptable excipient. Another preferred method for treating thrombotic disorder(s) in an individual comprises administering a peptide selected from the group consisting of: a) Y-S-D-G-D-Q-C; or b) C-F-D-K-I-K-N-W-R-N-L-I-A-V-L-G-E-H-D-L-S; or c) L-G-E-H-D-L-S-E-H-D-G-D-E-Q-S-R-R-V-A-Q-V-I; or d) V-Y-T-R-V-S-Q-Y-I-E-W-L-Q-K-L; or e) V-R-F-S-L-V-S-G-W-G-Q together with a pharmaceutically acceptable excipient to an individual. In yet another preferred embodiment, an individual may be treated for thrombotic disorder(s) by a method comprising administering the peptide, P-H-A-T-H-Y-R-G-T-W-Y-L-T-G-I, to the individual together with a pharmaceutically acceptable excipient. A fourth method for treating thrombotic disorder(s) made available by this invention comprises administering to an individual a peptide selected from the group consisting of: a) L-L-V-N-G-A-Q-L-C; or b) A-G-Y-S-D-G-S-K-D-S-C together with a pharmaceutically acceptable excipient. Any one of the peptides which are administered to an individual to treat thrombotic disorder(s) in that individual according to the invention may be used in conjunction with a plasminogen activator or other suitable thrombolytic therapeutic agent.

Finally, the invention includes a number of immunoglobulin preparations, wherein the antibodies or immunoglobulin molecules contained in these preparations are immunologically specific for (or immunologically reactive with the peptides of the present invention.

These and other aspects of the present invention will become more readily apparent when viewed in the context of the description of specific embodiments in the examples set below. However, neither the summary, the description or the examples are intended to limit the scope of the claims unless expressly stated herein.

DESCRIPTION OF THE DRAWINGS

FIG. 2(A-B). Dose-dependent inhibition of the rate of Factor Xa formation by Factor VII synthetic peptides initiated by the Factor VII-tissue factor complex. Tissue factor (0.05%), and Factor X (18 nM) were combined in the presence of varying concentrations of peptide and incubated for 30 min at 37 degrees Centigrade. Factor VII (0.2 pM) was added to initiate the reaction, and at various times, aliquots were removed and the Factor Xa activity measured in an amidolytic assay. Data are plotted as a percentage of the rate of Factor Xa formation determined in the absence of competing peptide, versus the final concentrations of the following peptides.

FIG. 4(A-D). Functional analysis of derivatives of known inhibitory synthetic peptides of Factor VII. Dose-dependent inhibition of the rate of Factor Xa formation was determined as a function of varying concentrations of derivatives of selected inhibitory peptides. To mixtures of tissue factor (0.05%) and Factor X (5 nM) was added varying concentrations of peptides followed by incubation for 30 min at 37 degrees Centigrade. The rate of Factor Xa formation was measured after the addition of Factor VII (0.2 pM). FIG. 4C: peptides 264-274 (solid circle), 276-286 (open circle), 285-294 (solid square), 285-305 (open square), and 290-299 (solid triangle); FIG. 4D: peptides 376-390 (circle) and 369-379 (square).

DESCRIPTION OF A PREFERRED EMBODIMENT

Figure 1:
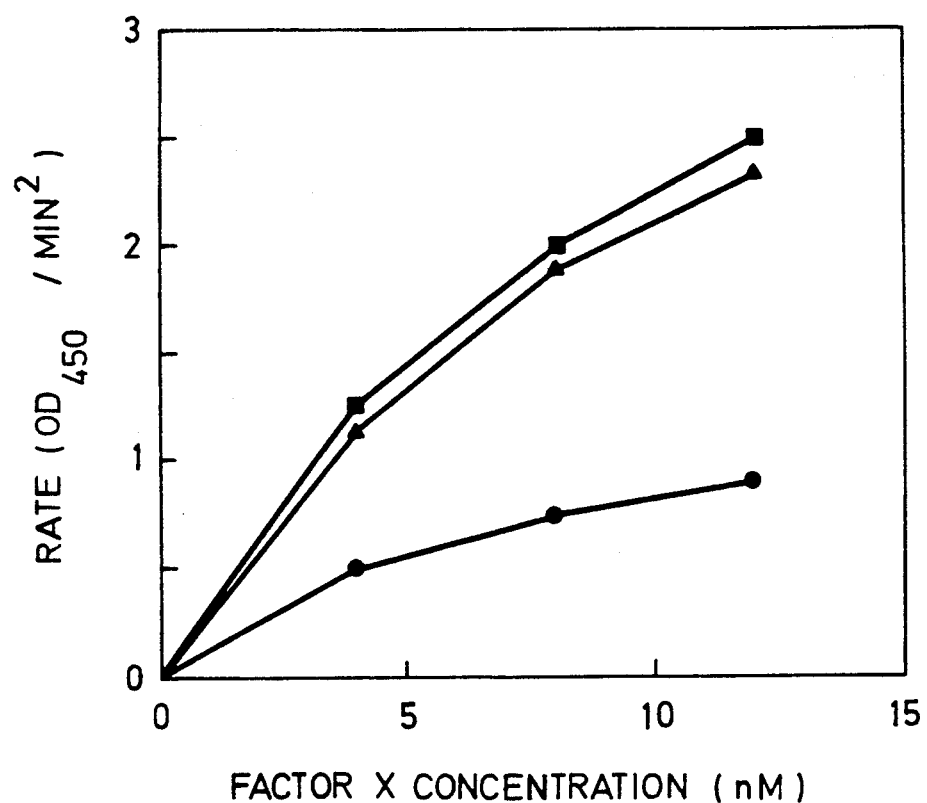
FIG. 1. The effect of selected synthetic peptides on the rate of Factor Xa formation as a function of the concentration of Factor X. To a mixture of tissue factor (0.05%), Factor X (varying concentrations), and 5 mM CaCl$_2$ was added either buffer (square) or 248 µM of peptide 226-243 (triangle) or 9.5 µM of peptide 285-305 (circle). The reactants were incubated for 30 min at 37 degrees Centigrade in order to achieve equilibrium for the peptide-protein interaction. Factor VII was then added (0.2 pM). Aliquots of the reaction were withdrawn at various times and the rate of Factor Xa generation was measured in a kinetic chromogenic assay (OD 405/min/min).

The present invention provides a number of novel antihemostatic peptides that are highly efficacious and specific. In addition, the peptides of the present invention are believed to be considerably less toxic than many anticoagulants used in the past. Finally, the peptides are not likely to induce undesirable immunologic side effects.

The coagulation inhibitory-peptides encompassed by the present invention are characterized by the ability to inhibit the function of Factor VII by preventing the association of Factor VII to tissue factor or by preventing the function of the assembled Factor VII-tissue factor complex to cleave Factor X, the substrate of the enzyme, by at least about 40%, when tested using the chromogenic assay set forth herein. Furthermore, with the aid of the present disclosure, additional assays suitable for determining inhibition of coagulation may be devised. For example, Factor IX, another substrate of the Factor VII-tissue factor macromolecular complex could be shown to be inhibited by the same set of claimed peptides.

With the aid of the present disclosure, one may obtain a number of effective peptides, however, the present inventors have shown that certain peptides are strikingly effective. Accordingly, peptides corresponding to amino acids located at or around position 206–229 and 285–305 of the Factor VII molecule using the numbering system set forth in Table I are preferred. Suitable peptides may comprise varying lengths, for example, from about 10 to about 35 amino acids, so long as they are capable of mediating the inhibition desired.

The inventors have characterized at least eight peptides of Factor VII that are highly effective at inhibiting the rate of Factor X activation and have discovered that regions represented by the eight peptides are involved in either the association of Factor VII with tissue factor or in association with one of the substrates, Factor X. These findings enable preparation of other effective peptide inhibitors that fall within the scope of the present invention. Therefore, although peptide 36–50, peptide 170–178, peptide 194–214, peptide 208–229, peptide 285–305, peptide 330–340, and peptide 376–390 all significantly inhibit the rate of Factor Xa formation in a dose-dependent manner and are preferred peptides for use in accordance with the present invention, a number of other peptides within the regions extending from amino acid 36 to amino acid 50, amino acid 194 to amino acid 229, amino acid 264 to amino acid 305, and amino acid 369 to 390, may all be suitable anticoagulants.

The inventions have also characterized a Factor VII peptide that effectively inhibits Factor Xa. This peptide inhibitor also falls within the scope of the present invention. Although peptide 4 347–361 can competitively inhibit Factor Xa activity in a dose-dependent manner, other peptides of increased or decreased size may also be suitable to inhibit Factor Xa function.

In addition, it will be readily appreciated that the peptides set forth herein may be modified or derivatized in a variety of ways that will not significantly affect their anticoagulant function. Such modifications may include, for example, conservative amino acid substitutions, amino acid modifications (including, for example, amidation of the carboxyl terminus and acetylation of the amino terminus), conjugation of the peptide to a selected carrier molecule, or other alterations, such as deletion or addition of amino acids, that do not significantly affect the peptides' anticoagulant properties. Such modified peptides are considered to fall within the scope of the present invention.

The following examples illustrate more clearly the method used by the present inventors to demonstrate the activity of a number of the peptides of the present invention using a model in vitro system.

Example I

DEMONSTRATION OF THE ACTIVITY OF THE PEPTIDES OF THE INVENTION IN IN VITRO SYSTEMS

A. Experimental Methods Used

1. Materials: Factor VII/VIIa (6), Factor X (7), and Factor Xa (8) were isolated as previously reported. Tissue factor was prepared from human brain as described (9) and was kindly provided by Dr. James H. Morrissey (Research Institute of Scripps Clinic, La Jolla, CA). The t-butyloxycarbonyl (Boc)amino acid derivatives were obtained from Chemical Dynamics Corp. (South Plainfield, N.J.) and Peninsula Laboratories, Inc. (Belmont, Calif.) and 9-Fluorenylmethoxycarbonyl (Fmoc) amino acid derivatives were bought from Milligen/Biosearch. (Bedford, Mass.), Calbiochem (La Jolla, Calif.) or Peninsula Laboratories. Glutaraldehyde (25%), cyanogen bromide, keyhole limpet hemocyanin (KLH), rabbit brain phospholipids (cephalin) were purchased from Sigma Chemical Company (St. Louis, Mo.). Protein A-agarose, Sepharose 4B and Sephadex G-25 were obtained from Pharmacia Fine Chemicals (Piscataway, N.J.). The chromogenic substrate for Factor Xa, CBS 31.39 ($CH_3SO_4$ D-Leu-Gly-Arg-pNA AcOH) was bought from American Byproducts Company (Parsippany, N.J.). Protein A-agarose, papain-agarose, bicinchoninic acid, Bis(sulfosuccinimidyl) suberate ($BS^3$), m-maleineidobenzylsulfosuccinimide (sulfo-MBS) and the IODO-GEN iodination reagent were obtained from Pierce Chemical Company (Rockford, Ill.). All other reagents were of the highest quality available.

2. Peptide synthesis and characterization: Amino acid sequences corresponding to the primary structure of Factor VII, numbered according to Hagen et al (10), are listed in Table I. Selected peptides were modified by the addition of glycyl and cysteinyl residues as indicated. The peptides listed in Table I were synthesized by Merrifield solid-phase methodology as described by Glass (11). Synthesis was performed on a Biosearch SAM II Synthesizer at the one mequiv scale. All residues were double-coupled using a 3-fold molar excess of each Boc-amino acid derivative to benzyhydrylamine resin. Deblocking was performed with 30% trifluoroacetic acid (TFA) in dichloromethane for 30 minutes. Peptides were cleaved from the resin and side-chained deprotection achieved by treatment with anhydrous hydrofluoric acid (HF) containing 20% anisole for 45 min at 0 degrees Centigrade. Peptides containing histidine were also treated with 2-mercaptoethanol before HF cleavage to remove the dinitrophenyl (DNP) side-chain protecting group. All subsequent peptides were made manually using the Fmoc chemistry and a RAMPs peptide synthesizer (DuPont Biotechnology, Inc. Wilmington, Del.) following the manufacturer's protocols for synthesis and cleavage.

All peptides were initially gel filtered on a BioRad P-2 column (2.5×83 cm) equilibrated in 1% acetic acid. Subsequent analysis and purification was performed on a Perkin-Elmer HPLC system using a Vydac C4 (2.1×25 cm, 5 micron) column equilibrated in 0.1% TFA and developed with a linear gradient of 0-50% acetonitrile over 50 minutes. The compositions and concentrations of isolated peptides were determined by subjecting them to 24 hour hydrolysis in 6 N HCl in evacuated tubes at 110 degrees Centigrade and by subsequent analysis on a Beckman Model 6300 Amino Acid Analyzer (Beckman Instruments, Fullerton, Calif.).

hydrolysis ($OD_{405}$/min) versus time and expressed as $OD_{405}/min^2$.

4. Coagulation assays: The effect of the synthetic peptides and antibodies to them on Factor VII coagulation activity was determined using two-stage clotting assays specific for Factor VII function.

Synthetic peptides were individually preincubated with 20 μl each of plasma immunochemically depleted of Factor VII and 0.25% tissue factor at 37 degrees Centigrade in a total volume of 190 μl adjusted with TBS containing 1% BSA and 5 mM $CaCl_2$. At the end of 30 minutes, coagulation was initiated by the addition of 10 μl of Factor VII (1 nM). The time for clot formation was measured using a Fibrometer (BBL, Cockesysville, Md.). Factor VII activity in the presence of varying concentrations of peptide was quantitated by comparing their clotting times to a standard curve constructed from the log of the clot time versus the log of a known amount of Factor VII in the same reaction mixture without added peptide.

5. Inhibition assays: The inhibition of Factor VII

TABLE I

Effect of Synthetic Peptides Representing the Primary Structure of Human Factor VII on the Rate of Factor Xa Formation

| Peptide | Amino Acid Sequence | Factor Xa Formation (% of Control Rate) |
| --- | --- | --- |
| 44-50 | YSDGDQC | 0 |
| CG + 141-150 | (CG)LEKRNASKPQ | 100 |
| 147-157 | SKPQGRIVGGK | 100 |
| 156-164 | GKVCPKGEC | 97 |
| 170-178 | LLVNGAQLC | 56 |
| 194-214 | CFDKIKNWRNLIAVLGEHDLS | 5 |
| 208-229 + GC | LGEHDLSEHDGDEQSRRVAQVI(GC) | 0 |
| 226-243 + GC | AQVIIPSTYVPGTTNHDI(GC) | 86 |
| 246-262 | LRLHQPVVLTDHVVPLC | 83 |
| 262-279 | CLPERTFSERTLAFVRFS | NS |
| 285-305 + GC | GQLLDRGATALELMVLNVPRL(GC) | 0 |
| 303-329 | PRLMTQDCLQQSRKVGDSPNITEYMFC | 92 |
| 330-340 | AGYSDGSKDSC | 62 |
| 347-361 + GC | PHATHYRGTWYLTGI(GC) | 0* |
| 376-390 | VYTRVSQYIEWLQKL | 0 |
| 387-406 | LQKLMRSEPRPGVLLRAPFP | 98 |

Rate of Factor Xa formation was determined by an amidolytic assay using purified proteins and 200 μM of each synthetic peptide. Amino acid sequences are numbered according to Hagen et al (10). G and C in parenthesis are added glycyl and cysteinyl residues respectively, to the indicated peptides.
NS = not soluble:
* = inhibits Factor Xa amidolytic activity directly.

3. Rate of Factor X activation: The effect of the synthetic peptides on the rate of activation of Factor X was analyzed in a purified system employing chromogenic assays. For the inhibition experiments, peptides were diluted in 20 mM Tris-HCl, 150 mM NaCl, pH 7.4 (TBS) and preincubated with 10 microliters each of Factor X (180 nM) and tissue factor (0.075%) at 37 degrees Centigrade in a total volume of 140 microliters adjusted with TBS containing 1% bovine serum albumin (BSA) and 5 mM $CaCl_2$. After 30 minutes, Factor X activation was initiated by the addition of 10 microliters of Factor VII (2 pM). At defined timed intervals, 20 microliter aliquots were removed and added to a microtiter plate containing 80 microliters of 50 mM Tris-HCl, 225 mM NaCl and 10 mM EDTA, pH 8.2. Following sample collection, 50 microliters of 0.6 mM chromogenic substrate was added and the rate of change in the absorbance at 405 nm was monitored for 10 minutes using a Vmax Kinetic Microplate Reader (Molecular Devices, Inc., Palo Alto, Calif.). The rate of Factor Xa formation was calculated from the slope of linear regression of data plotted as a function of the initial rate of function was determined in the two-stage chromogenic assay described in Example I-A, 3. The peptides were initially screened at 200 μM added concentration. To determine the concentration of peptide required to inhibit the rate of Factor X activation by 50% ($CI_{50}$), peptides at various concentrations or buffer (TBS-BSA) were incubated with their respective complexes. Following the addition of Factor VII, the rate of Factor Xa generation was determined and the percent of Factor X activation in the presence of different concentrations of Factor VII peptides relative to buffer controls was calculated. Analogous determinations of the $CI_{50}$ values were measured in the specific coagulation assay outlined above. Factor VII activity in the presence of varying concentrations of peptide was measured by comparing the clotting times to a standard curve constructed from the log of the clot time versus the log of Factor VII concentration in the same incubation mixtures described for the peptides.

Kinetic analysis of multiple inhibitors known to be noncompetitive in nature was conducted holding the concentration of the first inhibitory peptide constant and varying the concentration of a second inhibitory peptide. The analysis for mutual exclusivity of the inhibitory peptides employed the methods adapted from Segel (12). In general, Dixon plots which generate parallel lines of regression indicate that activity of a given peptide mutually excludes that of another tested peptide and suggest that the peptides are spatially close to one another. Regression lines which intersect with one another indicate mutual non-exclusivity of one peptide to another, i.e. tested peptides act as regions which are spatially separate from one another.

6. Preparation, characterization and purification of polyclonal antibodies: Antibodies were raised against selected synthetic peptides coupled to KLH. Sulfo-MBS (1 mg) was dissolved in 15 μl of dimethyl formamide and mixed with 5 mg of KLH previously dissolved in 1 ml of 20 mM phosphate, 150 mM NaCl, pH 7.4 (PBS). After 30 minutes of incubation at ambient temperature, the low molecular weight reactant was separated from KLH-MBS by gel filtration using a Sephadex G-25 column (1×18 cm) equilibrated in PBS. This protein was incubated with 5 mg of a cysteine containing peptide for 3 hours at room temperature. The peptide-carrier conjugates (300 μg and 150 μl of PBS) were emulsified with an equal volume of Freund's complete adjuvant and injected intradermally into four sites, one over each limb. After two weeks, the conjugate was emulsified in Freund's incomplete adjuvant and injected subcutaneously into four sites, one over each limb. The animals were challenged every month thereafter and sera were collected weekly starting six weeks after the initial immunization.

Sera were tested for reactivity against Factor VII and free peptides, using a solid phase radioimmunoassay (13). Polystyrene microtiter plates were coated with the peptide or Factor VII at 2.5 μg/ml by incubating each well with 100 μl of the peptide or protein in PBS for 16 to 18 hrs at 4 degrees Centigrade. The plates were washed three times with PBS containing 0.5% Tween 20, 1 unit/ml aprotinin, 10 mg/ml BSA and 0.2% $NaN_3$ (SPRIA buffer). Non-specific protein binding sites were blocked by adding 1% (wt/v) BSA in PBS for 30 minutes at room temperature. After removal of this solution, 100 μl of rabbit non-immune or specific antiserum serially diluted in SPRIA buffer was added for 90 minutes at 37 degrees Centigrade. Following incubation, the solution was removed and the wells were washed three times with SPRIA buffer and incubated with 100 μl $^{125}$I-goat anti-rabbit IgG (0.1 μg/ml) for 90 minutes at 37 degrees Centigrade. The unbound radioactivity was removed, the plates were washed with SPRIA buffer and dried, and the wells were cut out and counted in a gamma counter.

Purification of IgG from rabbit antisera was achieved by affinity chromatography on protein A-agarose. Equal volumes of rabbit antiserum and 100 mM Tris-HCl, 2 M NaCl, 0.1% $NaN_3$, pH 9.0, were mixed and applied to a 12 ml protein A-agarose column. The column was washed with 4 column volumes of 50 mM Tris-HCl, 1 M NaCl, 0.05% $NaN_3$, pH 9.0 and the bound IgG was eluted with 2 column volumes of 100 mM glycine-HCl, pH 3.0. The concentration of IgG was determined by the bicinchoninic acid protein assay method using BSA as the standard (14). Specific antibodies were purified by passing the IgG fraction of each rabbit antiserum over a 10 ml column of Factor VII coupled to agarose by the CNBr activation method (15) at a concentration of 0.5 mg of Factor VII/ml of agarose beads. The antibody bound to the column was eluted with 100 mM glycine-HCl, pH 3.0, into tubes containing 2 M Tris. These fractions were pooled, concentrated using an Amicon P-10 membrane and dialyzed against PBS.

For selected studies, monovalent Fab fragments were prepared by papain digestion of the specific antibody. To each milligram of IgG in 20 mM sodium phosphate, 10 mM EDTA and 20 mM cysteine (pH 7.0) was mixed with 50 μl of papain-agarose beads and incubated for 5 hrs at 37 degrees Centigrade with constant agitation. After centrifugation to remove the insoluble enzyme, the supernatant was applied to a protein-A agarose column equilibrated in 10 mM Tris-HCl (pH 7.5). The column was washed with the same buffer and the unbound portion containing the Fab fragments was collected and quantitated as described above.

7. Inhibition of Factor VII binding to a tissue factor-expressing cell line. Human bladder carcinoma J82 cells were cultured to confluency ($2.6 \times 10^6$ cells) in 48-well culture plates as described by Fair and MacDonald (16). Cells were washed three times with 10 mM Hepes, 137 mM NaCl, 4 mM KCl and 11 mM glucose (pH 7.45) containing 10 mg/ml BSA and 5 mM $CaCl_2$ (Hepes buffer). Varying concentrations of synthetic peptides in 0.4 ml were incubated with the cells for 30 minutes at 37 degrees Centigrade. Factor VII was added to a final concentration of 0.5 nM and the mixture incubated an additional 60 minutes. Cells were washed three times and incubated with 0.25 ml of 0.34 μM Factor X. The rate of Factor Xa formation was measured using time points at 4, 8 and 16 minutes following Factor X addition using the chromogenic assay described above.

8. Inhibition of peptide binding to tissue factor expressed on J82 cells. Cells were cultured in 48-well tissue culture plates to confluency and washed three times with Hepes buffer. Varying concentrations of a monoclonal antibody (TF8-5G9) specific for tissue factor (17), or normal mouse IgG in 0.2 ml was added to the cells for 60 minutes at room temperature. A synthetic peptide representing the amino acid sequence 199-221 which contained a conservative amino acid substitution of a tyrosine for a tryptophan at position 201 was prepared. This peptide was labeled with $Na^{125}I$ using the IODO-GEN method (18) to a specific activity of $1 \times 10^6$ cpm/μg. The $^{125}$I-peptide 199-221 (10 μl) was added to the cell antibody cultures for 30 minutes. The crosslinking reagent, Bis(sulfosuccinimidyl)suberate, 5 μl of 0.2 mM solution was added and incubated for 10 minutes. The reaction was quenched by addition of 0.1 M Tris-HCl (pH 7.45). The cells were washed three times with the Tris buffer, lysed with 0.5 ml of 200 mM NaOH, 1% sodium dodecylsulfate, 10 mM EDTA and counted in a gamma counter.

B. Analysis of Inhibition of Factor VII Function Using Kinetic Chromogenic Assays Factor VII function results from a two-step mechanism. First, Factor VII must associate with tissue factor in order to form the active macromolecular complex and second, Factor VII activity within the macromolecular complex can be measured by the conversion of substrate to product, e.g. activation of Factor X. The peptides of the present invention were tested for their ability to inhibit Factor X activation by employing the two-stage chromogenic assay described in Example I-A, 3. Inhibition of Factor X activation measured by this assay detects both of the steps stated for Factor VII function. To verify the inhibitory effect of the synthetic peptides, each of the components were titrated. The concentration of Factor VII used in the assay was in excess relative to the nonproteolytic cofactor, tissue factor, and the rates of Factor Xa formation were shown to be linear over the 8 minutes of sampling. Factor X was titrated against the preformed Factor VII-tissue factor complex in the presence of at least $10^4$ molar excess of each peptide. Selected peptides were inoubated with tissue factor and Factor X for 30 minutes at 3 degrees Centigrade before the addition of Factor VII. This preincubation time was sufficient for the peptides to reach equilibrium with the target protein (13).

FIG. 1 shows that there was a hyperbolic increase in the rate of Factor Xa generation as a function of Factor X concentration in the absence and presence of synthetic peptides. No difference in these profiles were observed between buffer controls and noninhibitory peptides as exemplified by peptide 226-243. However, certain peptides were remarkably effective inhibitors of the rate of Factor Xa formation. Peptide 285-305 (9.5 μM) reduced the rate and extent of Factor X activation by about 50%. The concentration of Factor X used in the additional studies described below represent 5% of the Km concentration of the reaction and was utilized in order to enhance the detection of other potential inhibitory peptides.

In other experiments, the sixteen synthetic peptides of Factor VII primary structure set forth in Table I, were analyzed. Each synthetic peptide (200μM) was added to mixtures containing tissue factor, phospholipid, CaCl$_2$ and Factor X and mixed for 30 minutes at 37 degrees Centigrade. Factor VII was added and the rate of Factor Xa formation was determined (Table I). Surprisingly, five peptides completely inhibited the rate of Factor Xa formation relative to the control reactions. Those peptides included amino acid sequences 44-50, 208-229, 285-305, 347-361, and 376-390. Peptide 194-214 inhibited the reaction by 95%, and two other peptides, 170-178 and 330-340 were capable of inhibiting the reaction by about 40%. Peptides that inhibited Factor Xa generation by less than 25% were considered not significantly inhibitory at these relatively high peptide concentrations. In control experiments, peptide 347-361 inhibited Factor Xa amidolytic activity directly, indicating that the inhibition observed with this peptide may have been due to inhibition of the chromogenic assay and not inhibition of the function of Factor VII. All other inhibitory peptides prevented the conversion of Factor X to Factor Xa in this assay system.

Figure 2A:
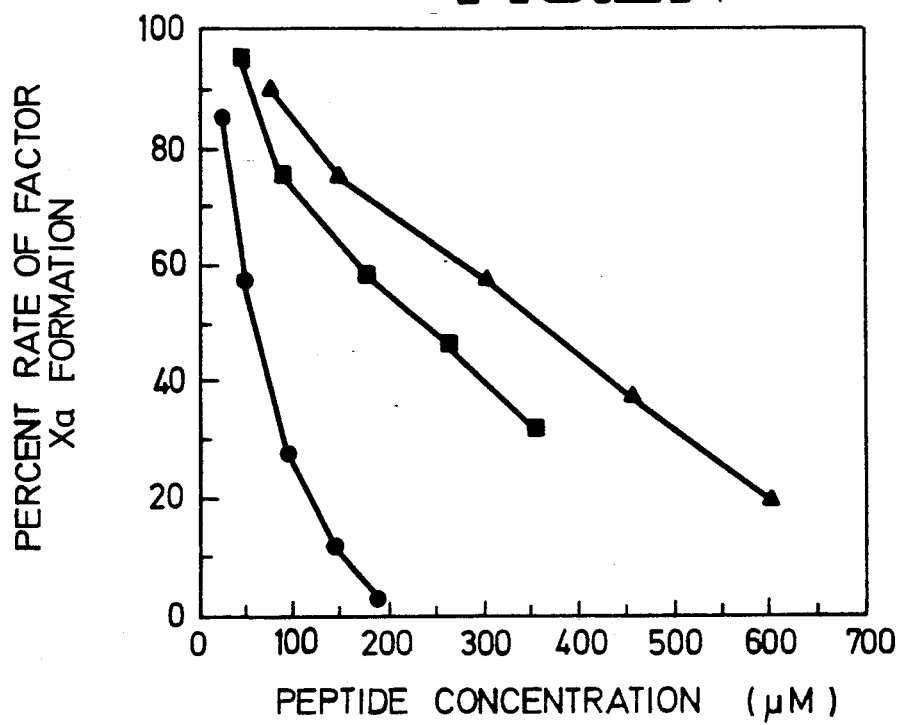
FIG. 2A; 44-50 (circle); 170-178 (square); 330-340 (triangle)
Figure 2B:
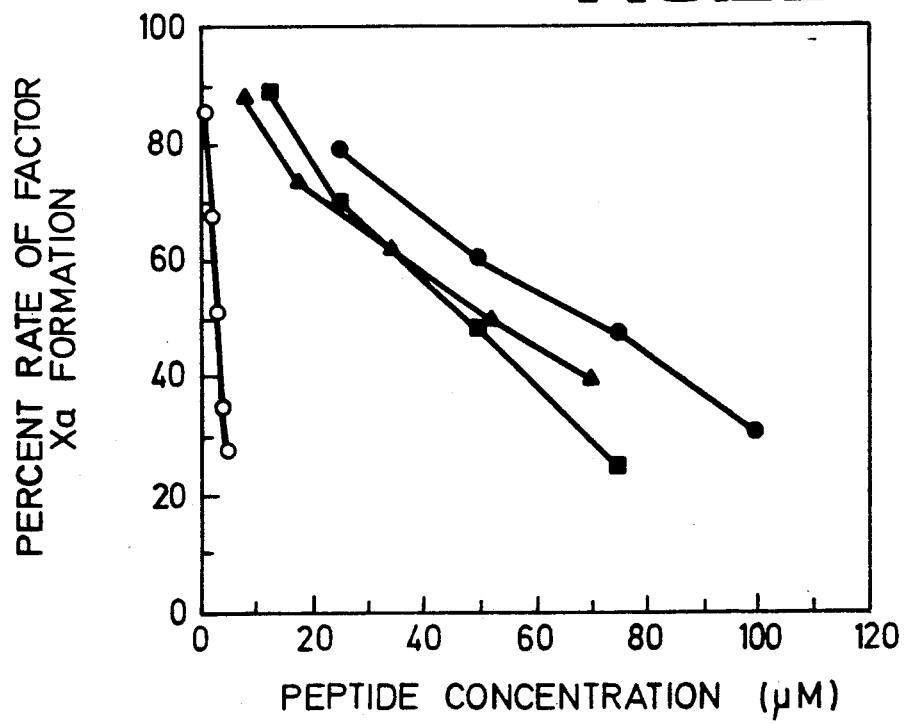
FIG. 2B; 285-305 (open circle); 208-229 (square); 376-390 (triangle); 194-214 (solid circle).
Figure 3A:
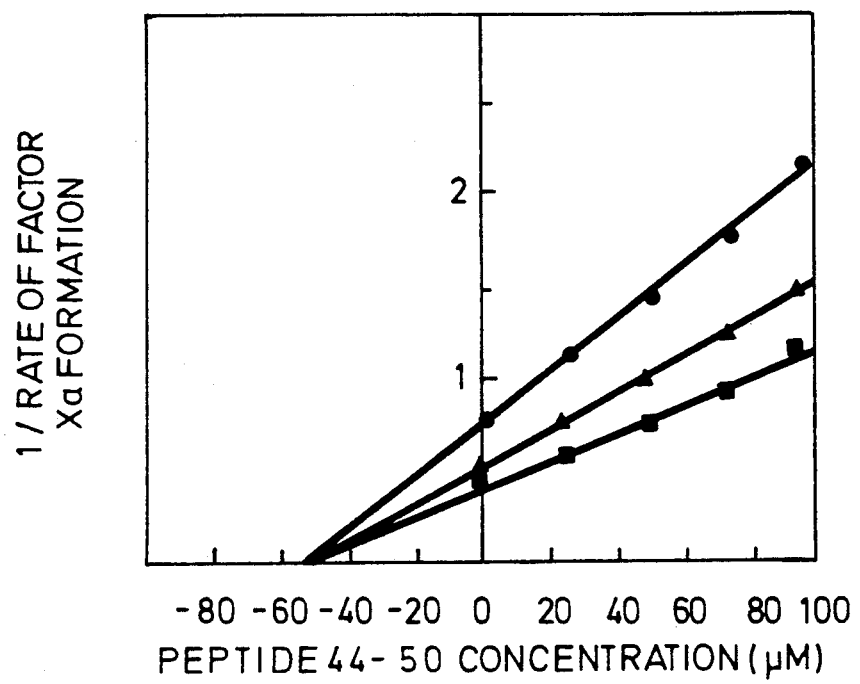
FIG. 3(A-H). Dixon plots of the inhibition of the rate of activation of Factor X by selected synthetic peptides: 44-50 3(A), 170-178 3(B), 194-214 3(C), 208-229 3(D), 285-305 3(E), 330-340 3(F), 347-361 3(G), and 376-390 3(H). The inverse of the rate of Factor Xa formation is plotted as a function of the final peptide concentrations for three concentrations of Factor X: 4nM (square), 8nM (triangle), and 12nM (circle).
Figure 3B:
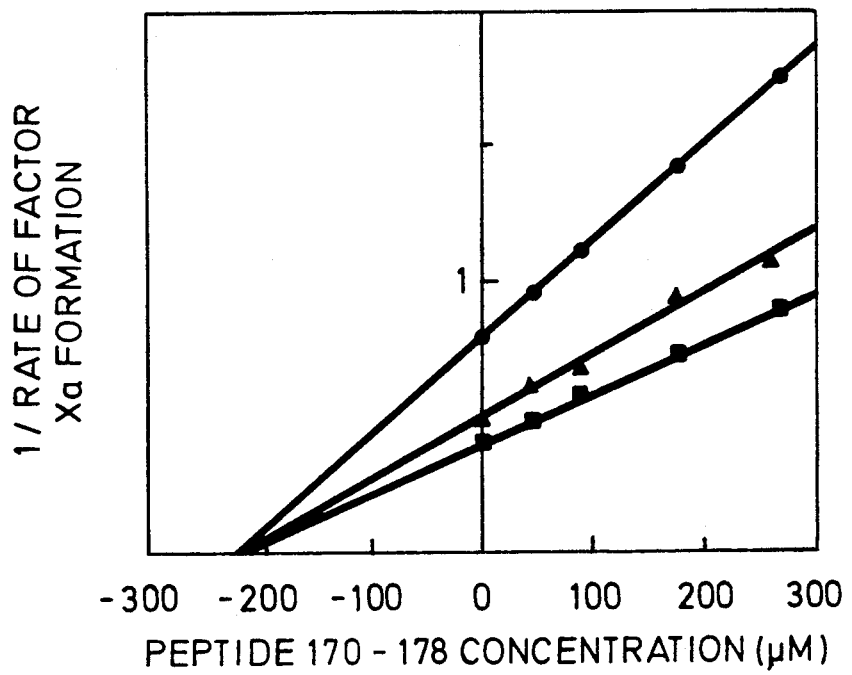
Figure 3C:
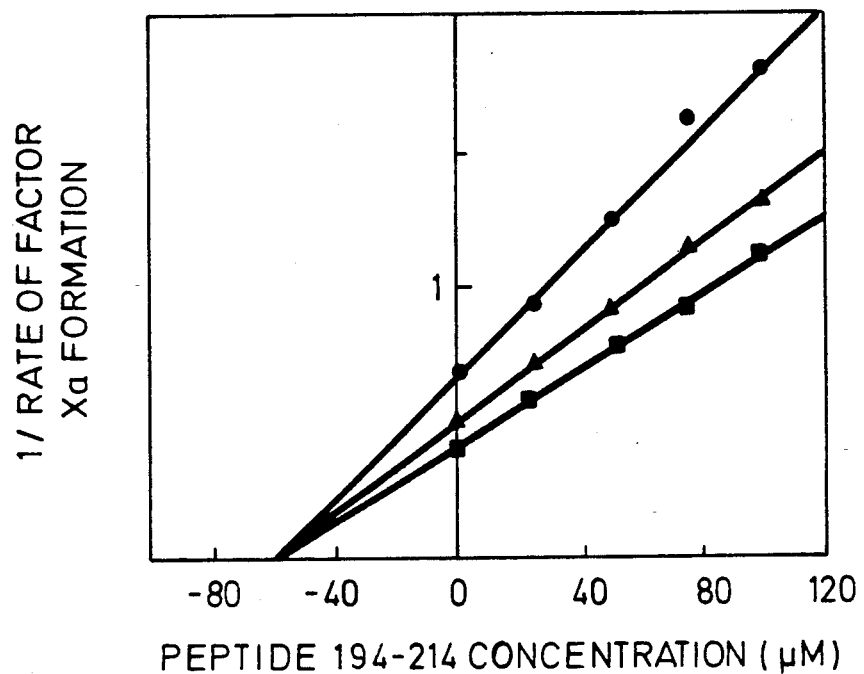
Figure 3D:
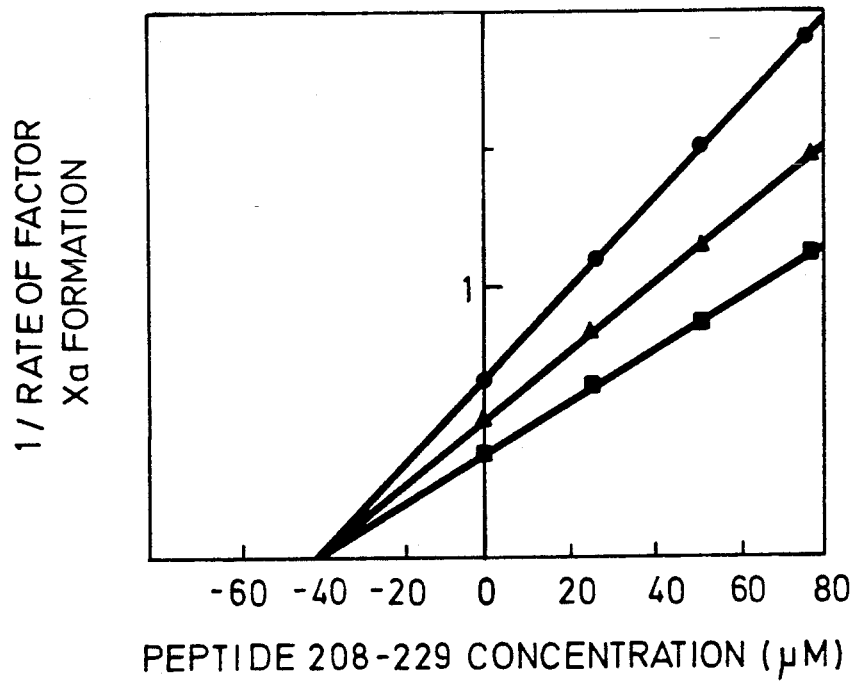
Figure 3E:
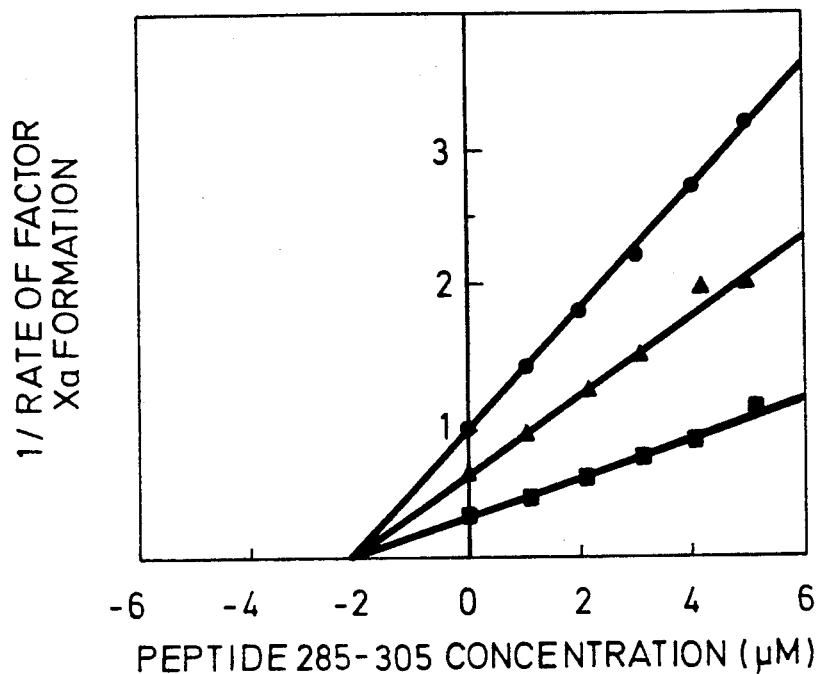
Figure 3F:
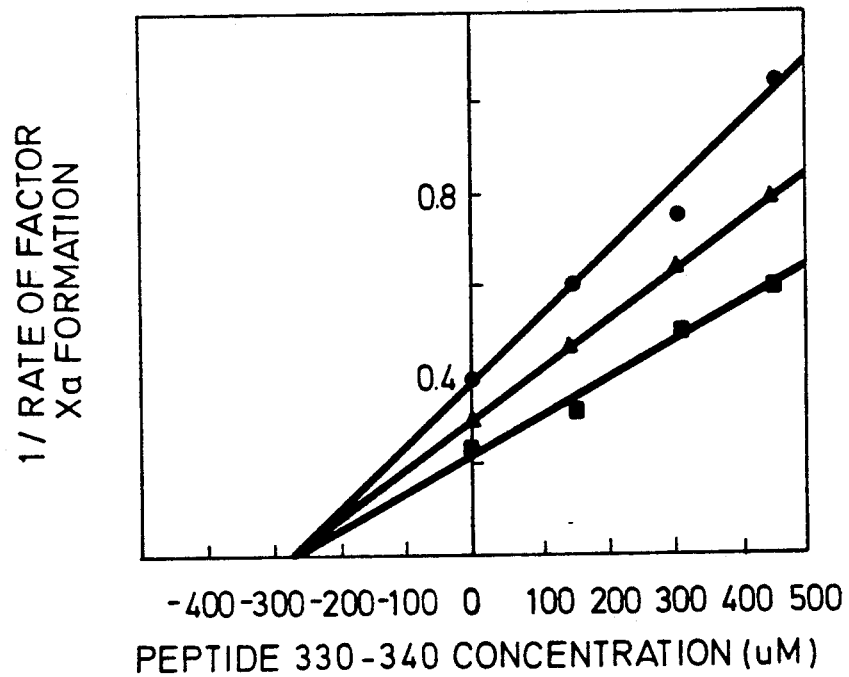
Figure 3G:
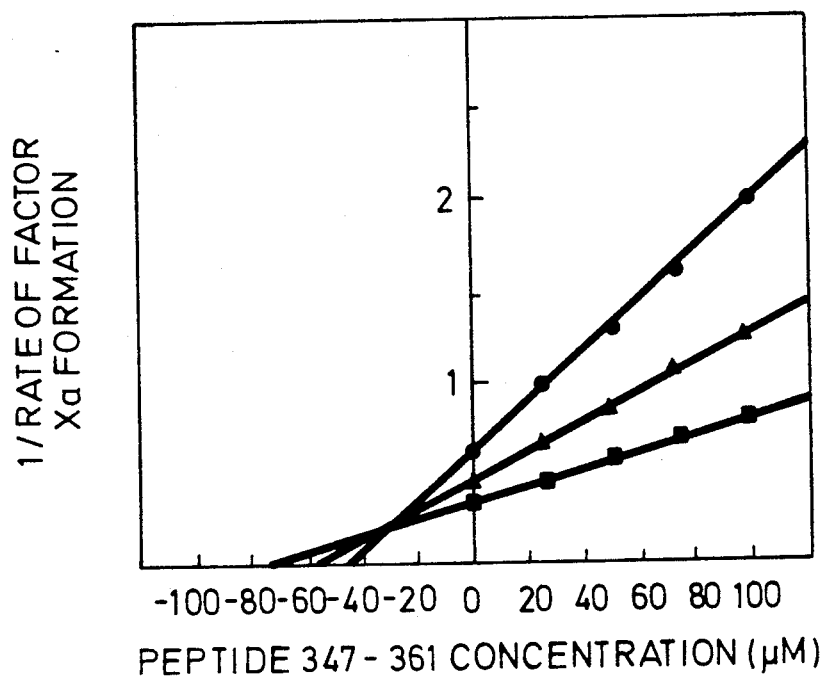
Figure 3H:
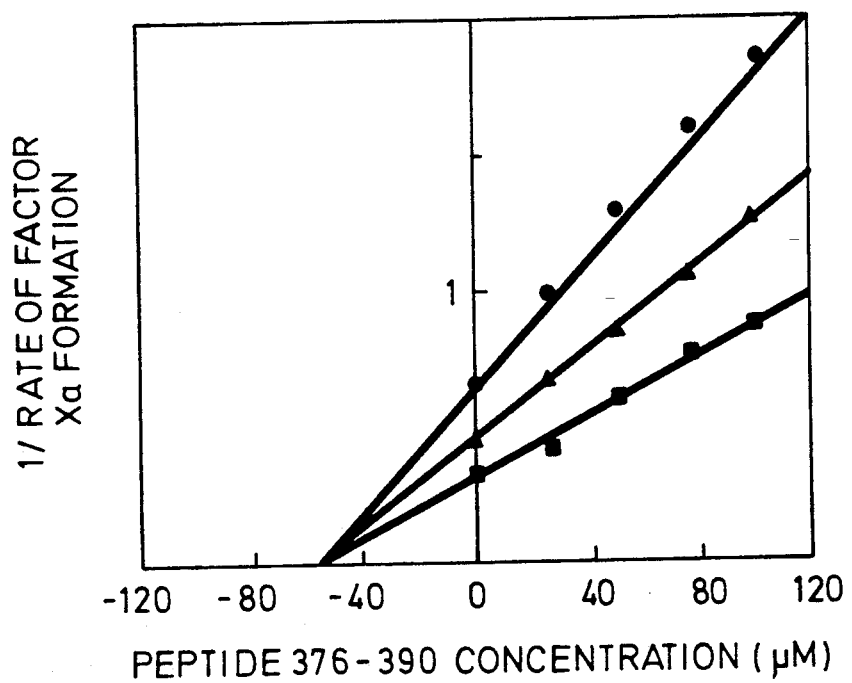

Dose-dependent inhibition by each of the remaining seven peptides was investigated (FIG. 2). Varying concentrations of each inhibitory peptide were incubated with tissue factor, Factor X, phospholipid, and calcium ions for 30 minutes at 37 degrees Centigrade, and, following the addition of Factor VII, the rate of Factor Xa formation was determined. The concentration of peptide 285-305 required for 50% inhibition was at least 15 to 20-fold less than that for peptide 44-50, 194-214, 208-229 or 376-390, and 75 to 100-fold less than that seen with peptides 170-178 and 330-340. A summary of the peptide concentration for 50% inhibition (CI$_{50}$) is shown in Table 2.

TABLE 2

Summary of the Inhibition of the Rate of Factor Xa Formation and Factor VIIa Coagulant Activity by Synthetic Peptides

| | Concentration for 50% Inhibition (μM)[a] | |
|---|---|---|
| Peptide | Rate of Factor Xa Formation | VIIa Coagulant Activity |
| 44-50 | 53 | ND* |
| 170-178 | 218 | ND |
| 194-214 | 68 | ND |
| 208-229 | 48 | 225 |
| 285-305 | 3 | 10 |
| 330-340 | 285 | ND |
| 347-361 | 34 | ND |
| 376-390 | 58 | 172 |

[a]The concentration of peptide which inhibited 50% of the rate of Factor Xa formation or the Factor VIIa coagulant activity is indicated.
*ND = not determined.

Each of the eight synthetic peptides was tested by the ability to interact directly with the active site of Factor VIIa or to act at a distal site. Varying concentrations of each synthetic peptide were mixed with tissue factor and three concentrations of Factor X, and, after addition of Factor VIIa, the rate of Factor Xa formation was determined. Dixon plots, the inverse of the rate of Factor Xa formation versus the final peptide concentration, for each of the eight inhibitory peptides tested are depicted in FIG. 3. Peptide 347-361 produced linear regression lines which intersected above the abscissa, a finding consistent with the peptide binding to the active site of Factor Xa in a competitive manner and thereby preventing cleavage of the chromogenic substrate. In Dixon plots of the other seven peptides, regression lines intersected on the abscissa, results consistent with a noncompetitive mode of inhibition, with inhibition occurring distal to the active site of Factor VIIa. The point at which each set of regression lines converged on the abscissa was used to calculate the apparent inhibitory constants (K$_i$) for each of the inhibitory peptides. Table 3 summarizes the K$_i$ values obtained. Again, the most inhibitory peptide was peptide 285-305 and the two least inhibitory peptides were 170-178 and 330-340.

TABLE 3

Peptide Inhibition Constants for Factor VII Activity

| Peptide | K$_i$ (μM)[a] |
|---|---|
| 44-50 | 54.9 ± 7.2 |
| 170-178 | 215 ± 11.8 |
| 194-214 | 61.1 ± 4.7 |
| 208-229 | 44.3 ± 5.6 |
| 285-305 | 2.8 ± 0.4 |
| 330-340 | 247 ± 13.9 |
| 347-361 | 35.2 ± 6.1 |
| 376-390 | 57.8 ± 8.3 |

[a]The K$_i$ values were determined from Dixon plots of the rate of Factor Xa formation.

These results indicate that the seven inhibitory peptides may impede the association of Factor VII with tissue factor, or alternatively, may prevent the association of Factor X with the assembled Factor VII-tissue factor complex. These results also confirm the result noted in Table 1 where peptide 347-361 interacts directly in a competitive manner with the active site of Factor Xa.

Figure 4A:
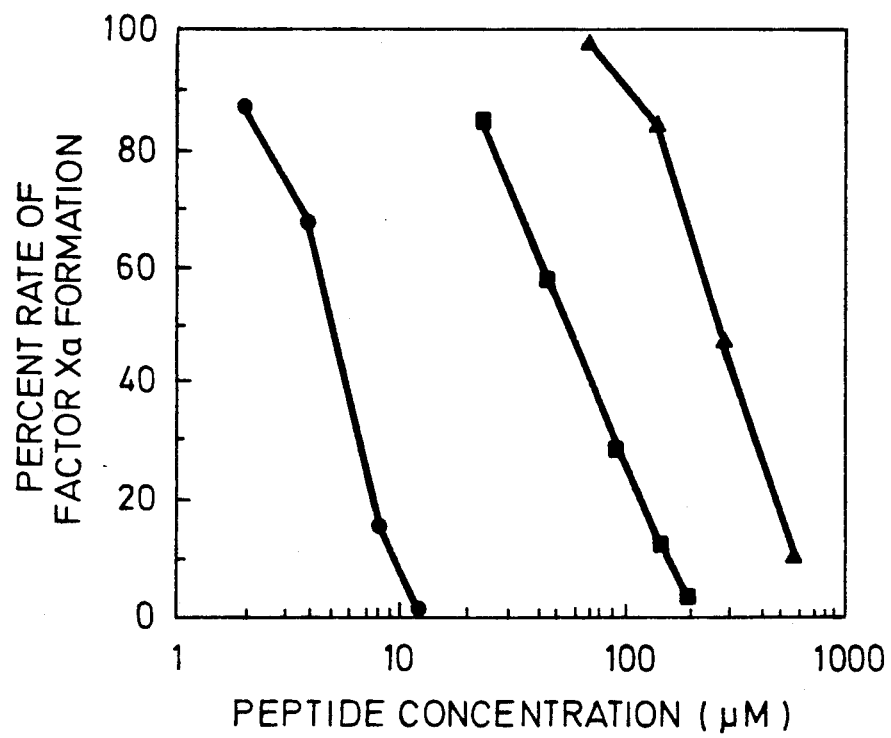
FIG. 4A: peptide 36-49 (circle), 44-50 (square), 43-49 (triangle)
Figure 4B:
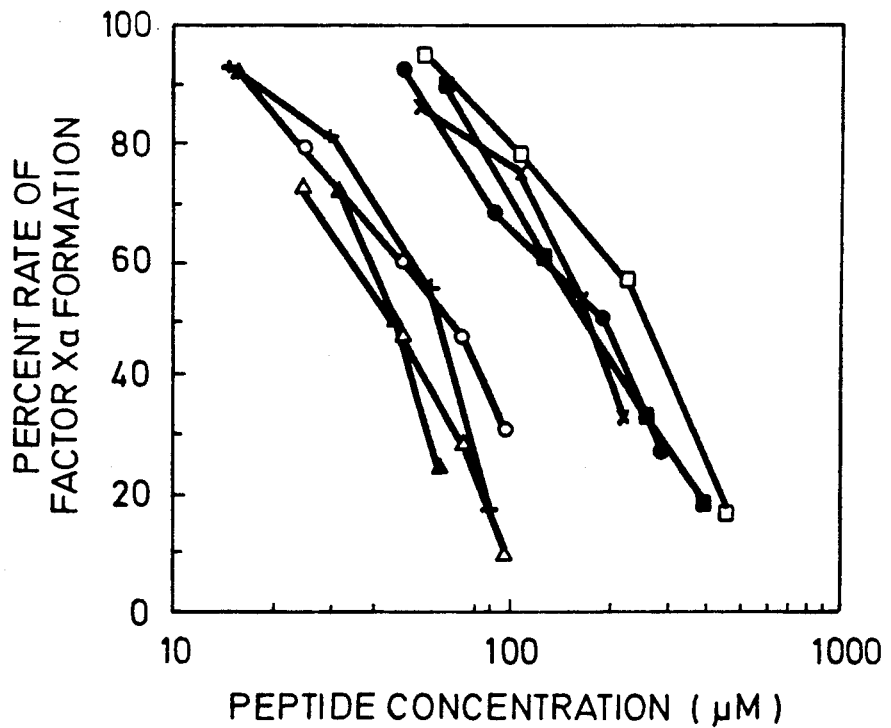
FIG. 4B: peptides 194-214 (open circle), 193-203 (solid circle), 196-206 (solid square), 202-214 (open square), 206-218 (solid triangle), 208-229 (open triangle), 209-221 (+), and 214-226(×)
Figure 5A:
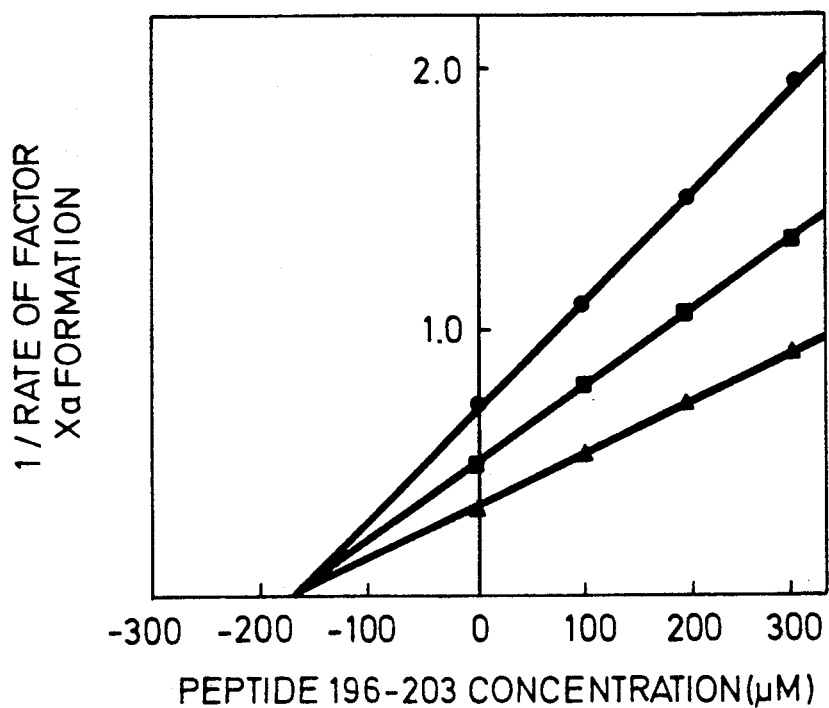
FIG. 5(A-K). Dixon plots of selected synthetic derivatives to inhibitory Factor VII peptides. The rate of Factor Xa formation is plotted as a function of peptide concentration for the indicated synthetic peptides. The concentration of Factor X in each analysis was as follows: Panel 3A, 3B, and 3(D-K) were 4nM (triangle); 8nM (square); and 12 nM (circle). Panel C was 4 nM (circle); 8 nM (triangle); and 12 nM (square).
Figure 5B:
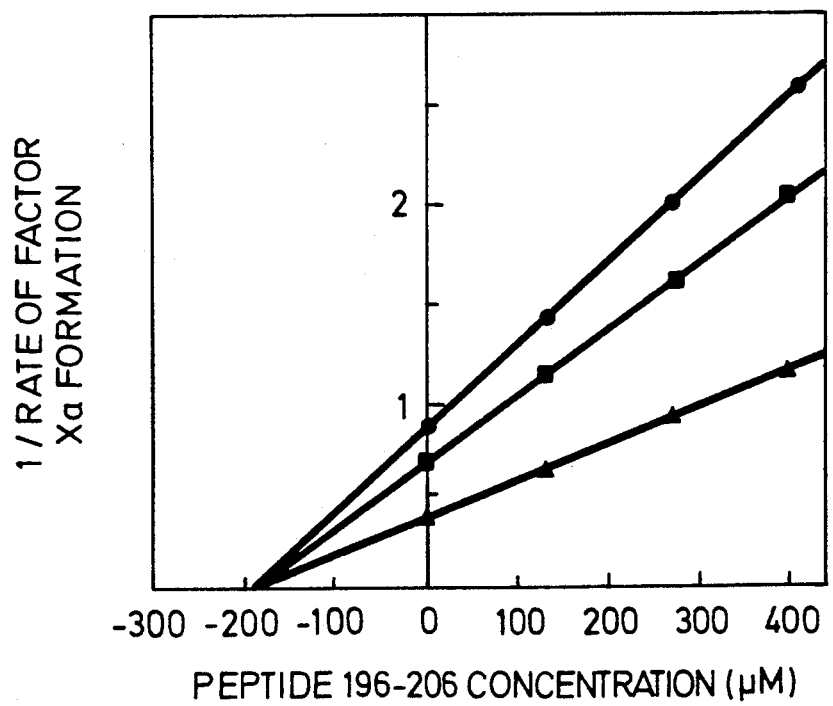
Figure 5C:
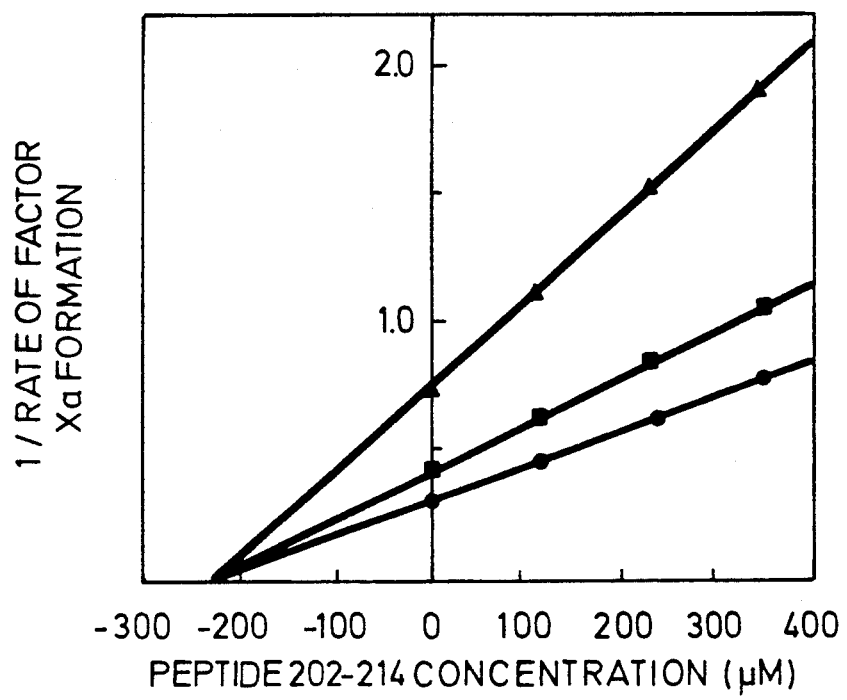
Figure 5D:
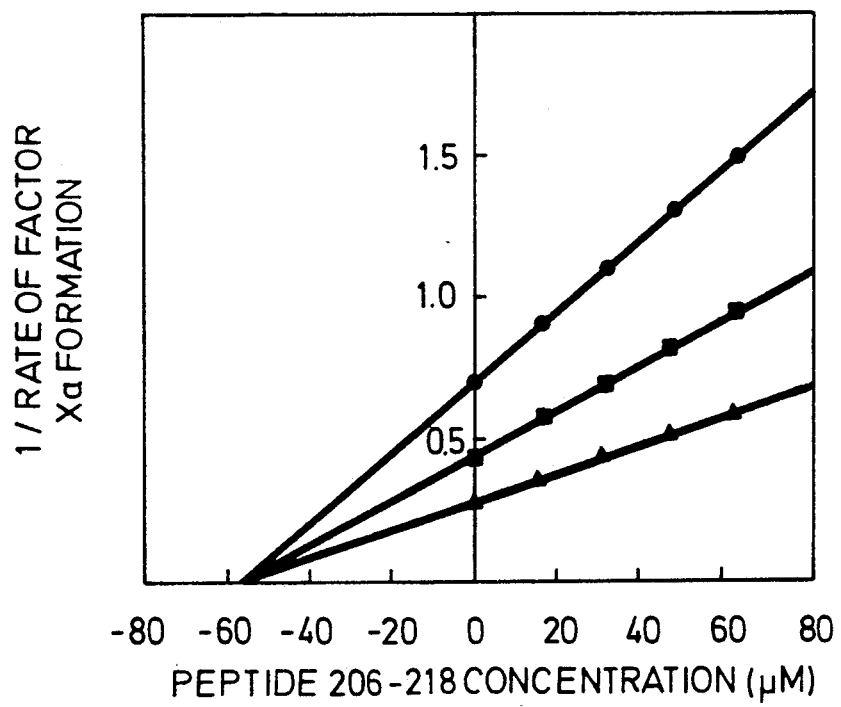
Figure 5E:
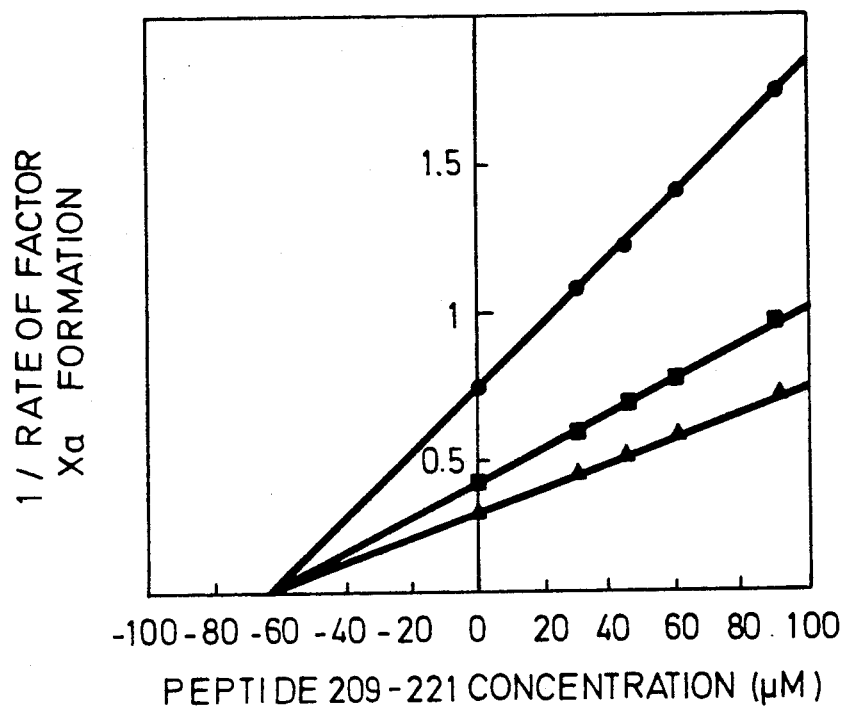
Figure 5F:
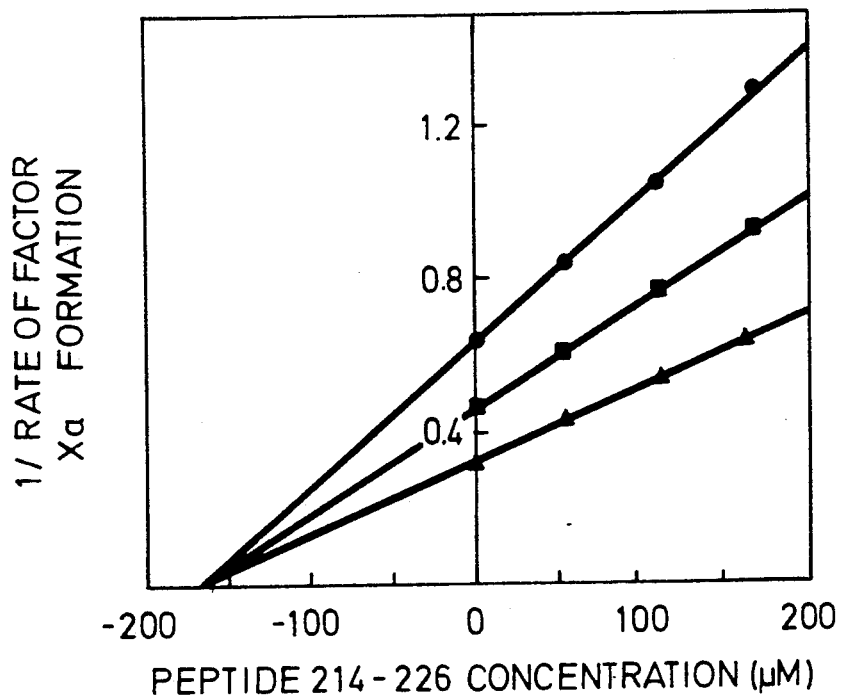
Figure 5G:
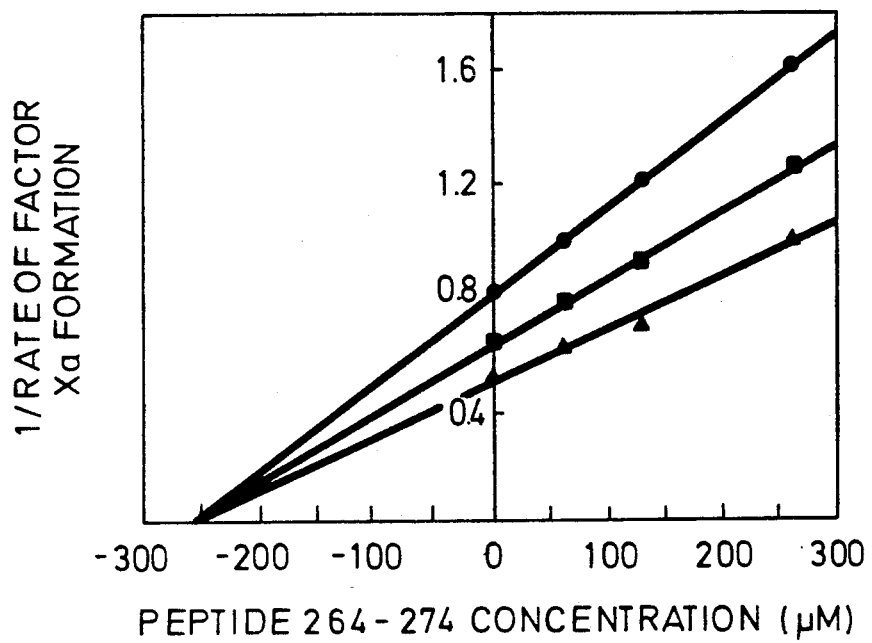
Figure 5H:
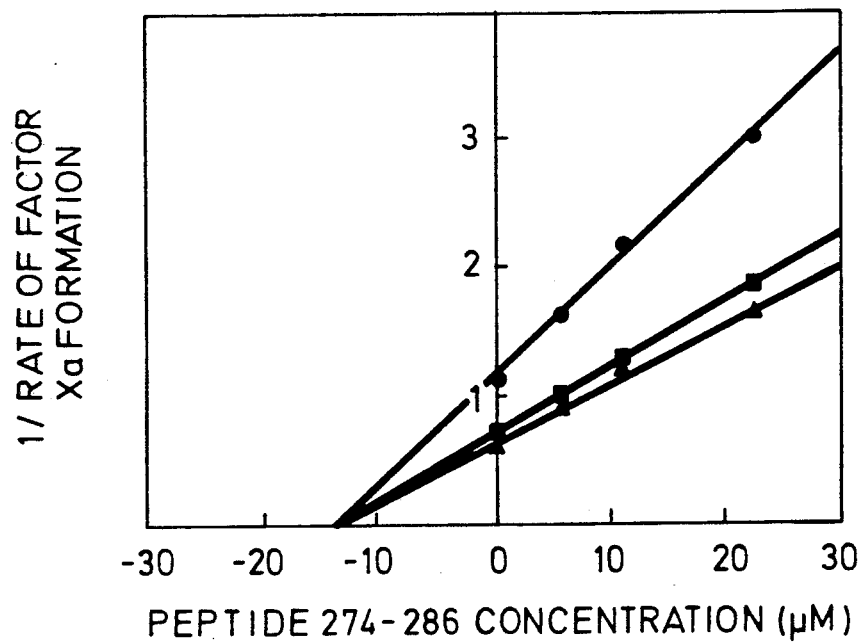
Figure 5I:
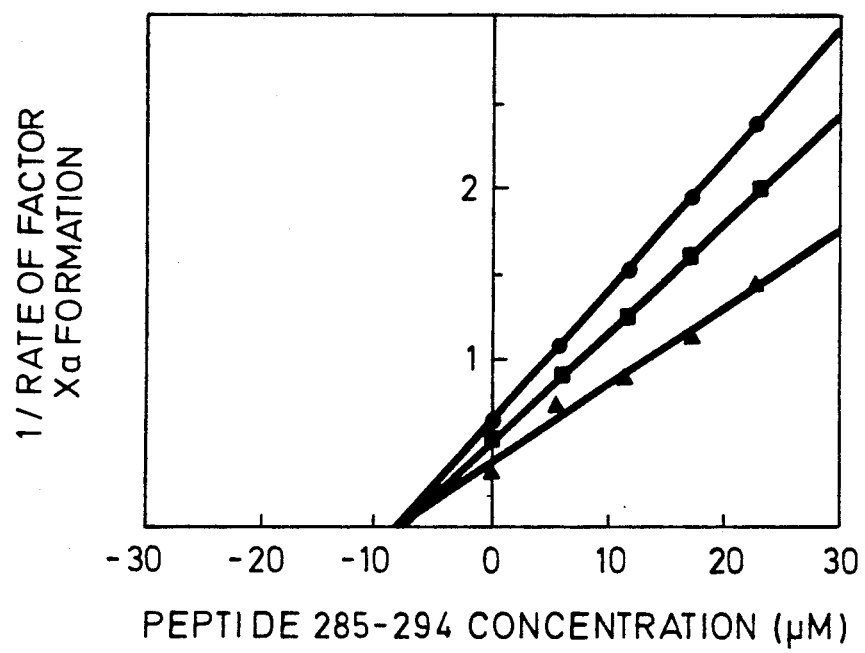
Figure 5J:
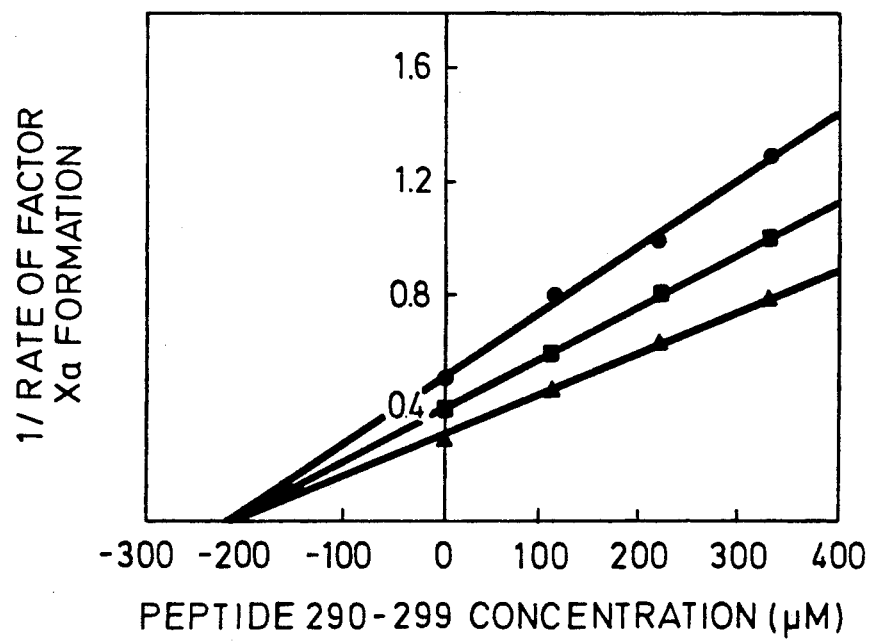
Figure 5K:
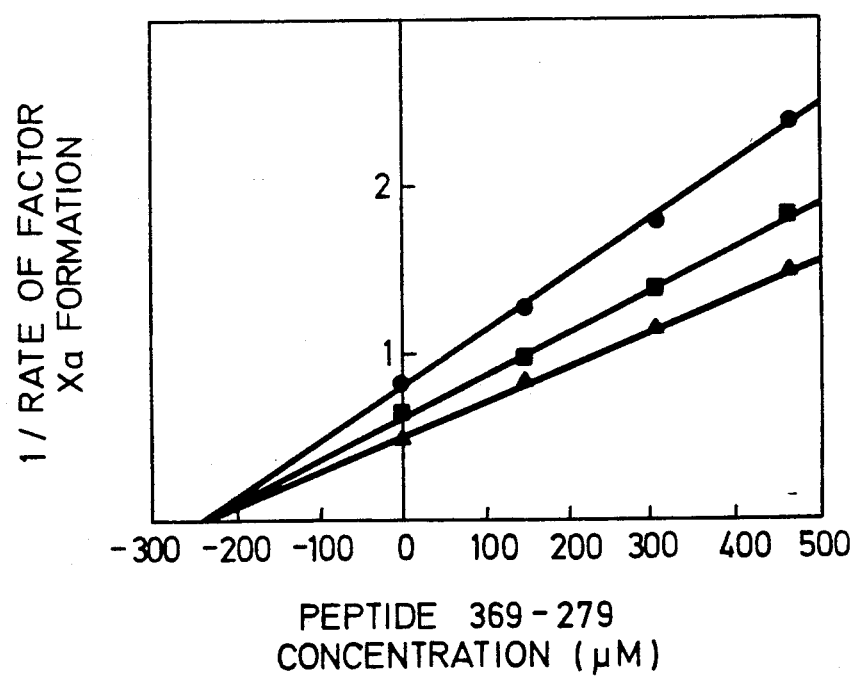

Additional experiments were performed in order to determine whether specific sequences within the peptides initially tested were important in mediating the inhibition of Factor Xa activation. Eighteen synthetic peptides were tested and shown to inhibit Factor VII activity in a dose-dependent manner (FIG. 4).

When derivatives of the peptide 194-214 were tested peptides 206-218 and 208-229 had the lowest apparent $CI_{50}$ values ($\approx 50$ μM). Peptides 194-214 and 209-221 GQLLDRGATALELMVLNVPRL and finally within the carboxy terminus of Factor VII the most inhibitory region is represented by a fifteen amino acid peptide 376-390 whose sequence is VYTRVSQYIEWLQKL.

TABLE 4

Inhibition of Factor VII Activity by Derivatives of the Inhibitor Synthetic Peptides

| Region | Peptide | Amino Acid Sequence | $CI_{50}(\mu M)^a$ |
|---|---|---|---|
| I | 36–49 | RTKQ$^b$FWISYSDGDQ | 6 |
|  | 44–50* | YSDGDQ | 53 |
|  | 43–49 | SYSDGDQ | 220 |
| II | 194–214* | CFDKIKNWRNLIAVLGEHDLS | 68 |
|  | 196–203 | DKIKNWRN | 196 |
|  | 196–206 | DKIKNWRNLIA | 185 |
|  | 202–214 | RNLIAVLGEHDLSE | 205 |
|  | 206–218 | AVLGEHDLSEHDG | 52 |
|  | 208–229 | LGEHDLSEHDGDEQSRRVAQVI | 48 |
|  | 209–221 | GEHDLSEHDGDEQ | 62 |
|  | 214–226 | SEHDGDEQSRRVA | 165 |
| III | 264–274 | PERTFSERTLA | 260 |
|  | 276–286 | VRFSLVSGWGQ | 16 |
|  | 285–305* | GQLLDRGATALELMVLNVPRL | 3 |
|  | 285–294 | GQLLDRGATA | 15 |
|  | 290–299 | RGATALELMV | 225 |
| IV | 369–379 | ATVGHFGVYTR | 230 |
|  | 376–390 | VYTRVSQYIEWLQKL | 58 |

$^a$The concentration of peptide inhibiting the rate of Factor Xa activation by 50%.
$^b$A glutamine was substituted for leucine to increase solubility of the peptide.
*Indicates original screening peptide.

inhibited the rate of Factor Xa formation slightly less ($CI_{50}\approx 70$ μM). Other derivative peptides were 3 to 4-fold less inhibitory by this assay. Because of these differences in apparent $CI_{50}$ values, the minimal amino acid sequence which inhibits the reaction best was represented by the deduced 208-218 sequence. Other amino acids to the amino or carboxyl of this segment may play import auxillary functions which requires further study to confirm their potential role.

Analysis of the peptide region 285-305 indicated that this peptide was the most inhibitory and derivatives of the peptide, which included amino acids either to the amino or carboxy terminus of its sequence, showed an increase in the apparent $CI_{50}$ value of about 5-fold (FIG. 4). Other derivatives showed lower ability to inhibit the rate of Factor Xa formation. These data indicate that the sequence represented by peptide 285-305 contains the amino acid residues primarily responsible for the inhibition of Factor VIIa function.

Other derivatives at the carboxy terminus of Factor VII represented by peptide 376-390 inhibited the activation of Factor X better than peptide 369-379. Thus, in addition to some cases where the original peptide was the most inhibitory for Factor VII activity, other derivatives proved to contain more potent inhibitory sites either due to increased solubility of the peptide or inclusion of amino acids which appeared to interact with either the cofactor, tissue factor, or the substrate, Factor X.

A summary of the $CI_{50}$ values of the derivative synthetic peptides is shown in Table 4. The amino acid sequences are also given to help identify the minimal amino acid sequence required for maximum inhibition. As seen in Table 4 for region I, peptide 36-49 was the most inhibitory containing fourteen amino acids with the sequence RTKQFWISYSDGDQ. For region II the most inhibitory area can be deduced to be the sequence 208-218 containing eleven amino acids with the sequence LGEHDLSEHDG. For region III the original peptide 285-305 Was the most inhibitory and included twenty-one amino acids with the sequence As shown in FIG. 5, each of the derivatives of the peptides inhibited Factor VII in a noncompetitive manner. Varying concentrations of selected synthetic peptide derivatives were incubated with tissue factor and three concentrations of Factor X for 30 minutes at 37 degrees Centigrade. After the addition of Factor VII the rate of Factor Xa formation was determined and the data were analyzed by Dixon plots. In each case linear regression lines were obtained which intersected at the abscissa indicative of non-competitive inhibition confirming the original observation of a non-competitive inhibitory mechanism.

Mixed inhibition experiments were performed to further characterize the mode of inhibition. FIG. 6 depicts the results of two experiments where varying concentrations of peptide 209-221 (region II) were mixed with a fixed concentration of either peptide 285-305 (region III) or peptide 193-203 (region II). After incubating the peptides with tissue factor and Factor X, Factor VII was added, and the rate of Factor Xa formation determined.

Figure 6A:
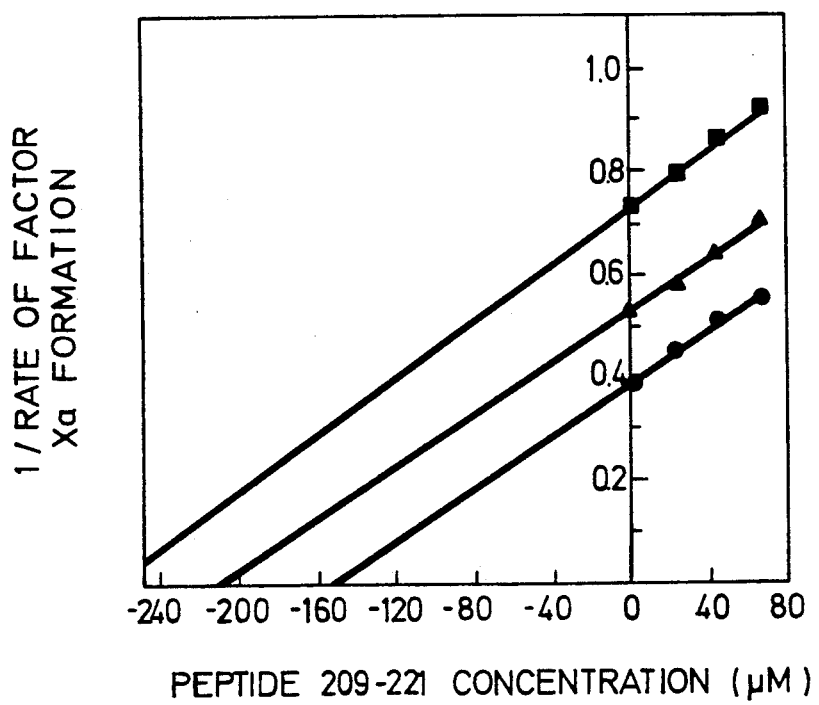
FIG. 6(A-B). Dixon plots of the inhibition of the rate of Factor Xa formation by a mixture of inhibitory peptides. The inverse of the rate of Factor Xa formation is plotted as a function of peptide 209-221 concentration in the presence of constant concentrations of: Top panel(6A); peptide 193-203 at 0 (circle), 14 (triangle) and 28 (square) µM; or Bottom Panel(6B), peptide 285-305 at 0 (circle), 1.5 (triangle) and 3.0 (square) µM.

In FIG. 6A the regression lines resulting from mixed inhibition of peptides 209-221 and 193-203 were parallel indicating that those peptides are mutually exclusive of one another. In toto, the results obtained suggest that the two areas on Factor VII are located close to each other, and represent a single association site for Factor VII.

Figure 6B:
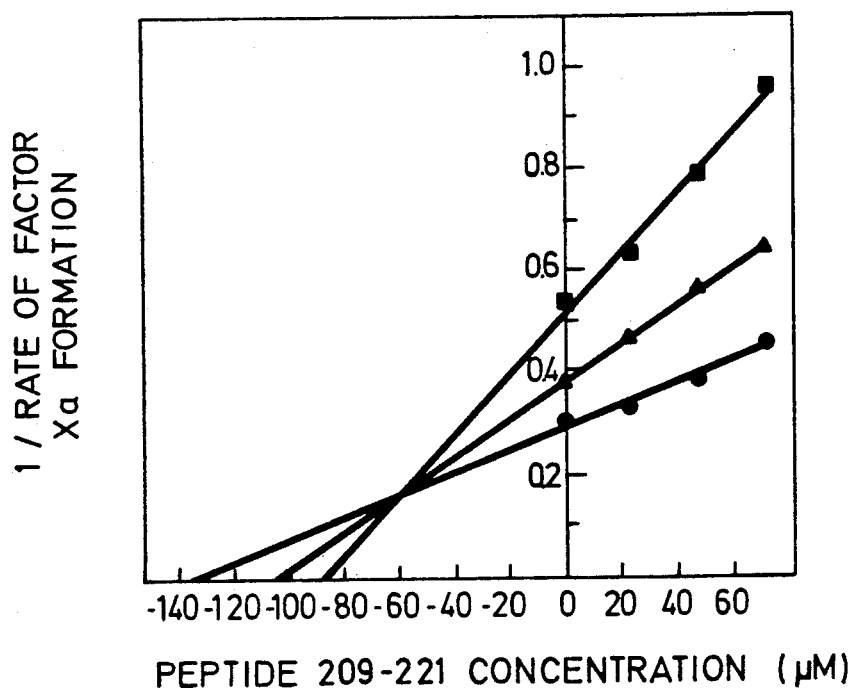

FIG. 6B shows that when peptides 208-221 and 285-305 were analyzed, the three regression lines intersected with one another above the abscissa, indicating a lack of mutual exclusively among the peptides. This result suggests that the regions on Factor VII represented by the two peptides are distal to one another and represent two independent sites of interaction on Factor VII.

C. Peptide Inhibition of Factor VII Coagulant Activity

Figure 7:
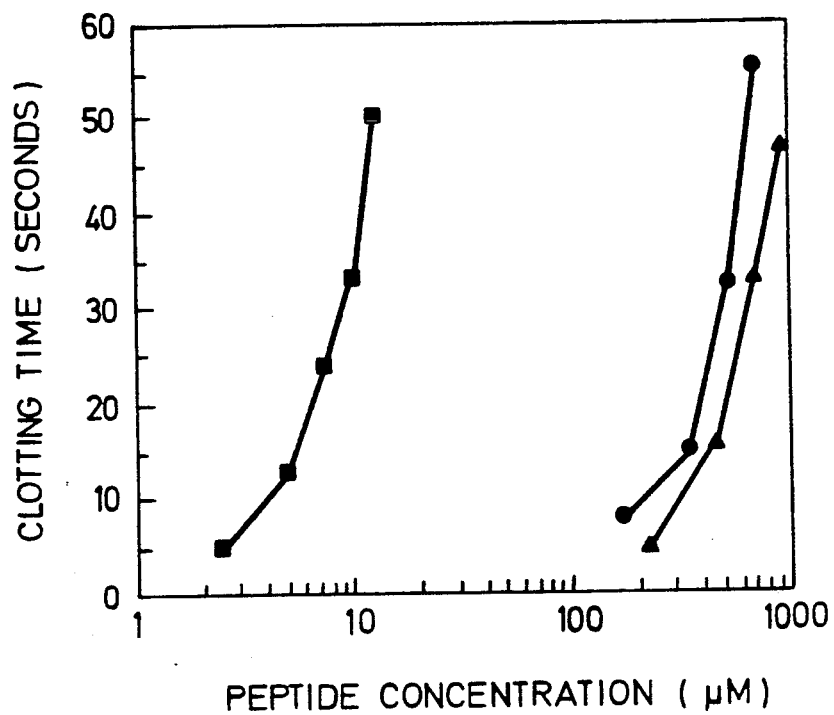
FIG. 7. Dose-dependent inhibition of Factor VII procoagulant activity. Factor VII deficient plasma containing tissue factor and calcium ions was incubated with various concentrations of peptides 209-221 (triangle), 285-305 (square) and 369-379 (circle) for 30 min at 37 degrees Centigrade. The clotting time was measured and plotted versus the peptide concentration.

Based on the results of the chromogenic assays, three peptides, 208-229, 285-305 and 276-390, were selected for further study for their ability to inhibit a coagulation-based assay designed to measure Factor VII activity. Varying concentrations of peptides were added to Factor VII-depleted plasma along with tissue factor and incubated for 30 minutes at 37 degrees Centigrade. After Factor VII was added, the time of clot formation was determined and quantitated. Each of the three peptides tested inhibited clot formation in a dose-dependent manner (FIG. 7), and the estimated $CI_{50}$ values were from 3 to 5-fold greater than those observed for the purified system using chromogenic assays. The $CI_{50}$ values have been summarized in Table 2.

D. Antibody-Mediated Inhibition of Factor VII Activity

In additional experiments, the inventors raised polyclonal antibodies to four synthetic peptides. Specificity of the antisera was shown by solid phase radioimmunoassay. The antibodies were purified by affinity chromatography on a Factor VII-agarose column, and, in some cases, Fab fragments were prepared as described in Example I-A, 6.

Figure 8:
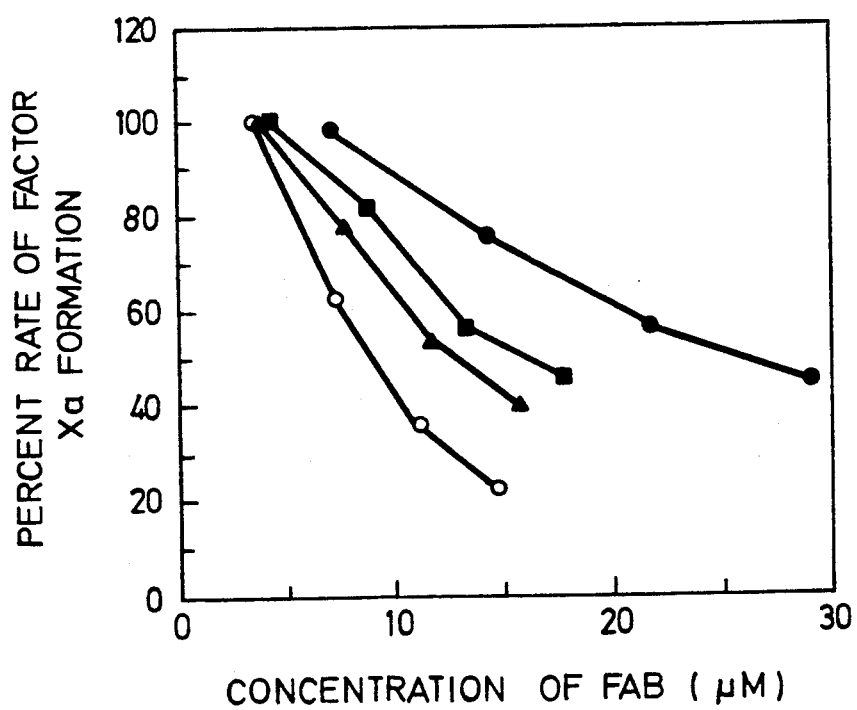
FIG. 8. Inhibition of Factor X activation by antibodies made to selected synthetic peptides. Rabbit antibodies raised to peptides 40-50 (solid circle), 170-178 (square), 208-229 (triangle), and 285-305 (open circle) were affinity purified on a Factor VII-agarose column. These antibodies were digested with papain, and the isolated Fab fragments were incubated with Factor VII for 15 min at 37 degrees Centigrade before assay. The rate of Factor Xa formation relative to the rate observed in the presence of nonimmune rabbit IgG is plotted versus the concentration of anti-peptide Fab fragment.

The Fab fragments were assayed for their ability to inhibit the rate of Factor X activation. The Fab fragments specific for each of the four peptides all inhibited the rate of Factor Xa formation in a dose-dependent manner (FIG. 8). The concentrations which yielded approximately 50% inhibition ranged from 8 to 25 μM and the Fab fragments from antibodies raised to peptide 285-305 were the most inhibitory. The fact that antibodies to these inhibitory peptides can react with Factor VII, supports the notion that the regions on Factor VII represented by these amino acid sequences are largely surface-exposed and are readily available to interact with tissue factor (cofactor), and Factor X (substrate) in addition to the antigen combining sites of Fab fragments.

E. Inhibition of Factor VII Activity on J82 Cells

Figure 9:
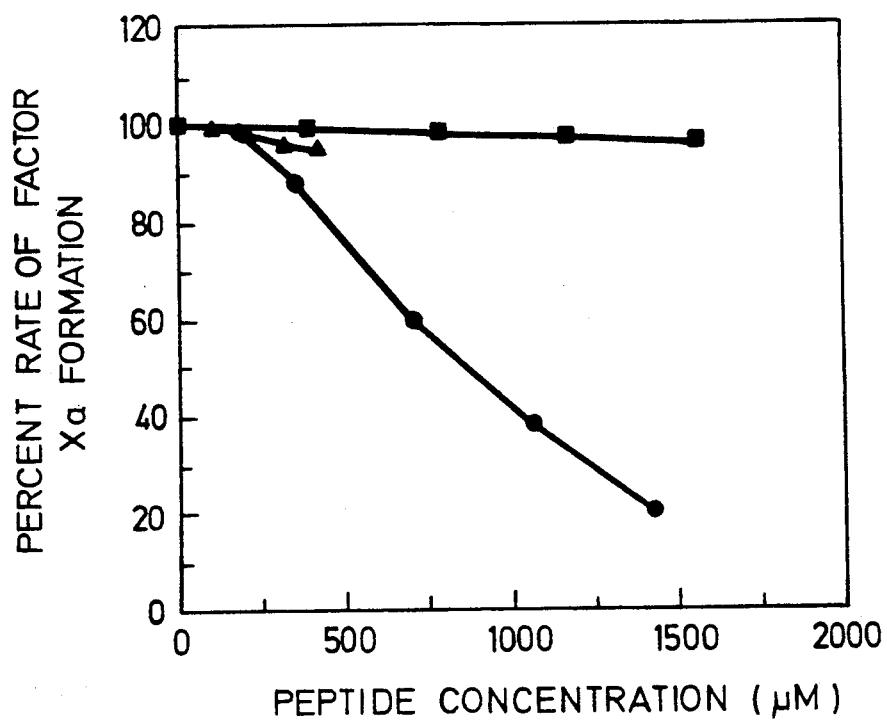
FIG. 9: Dose-dependent inhibition of Factor VII binding to a cell line expressing tissue factor. Monolayers of J82 cells were incubated in the presence of varying concentrations of synthetic peptide 206-218 (circle), 285-296 (triangle) or 330-340 (square) for 30 min at 37 degrees Centigrade. Factor VII (0.5 nM) was added to the cultures for 60 min and then removed by washing. Factor X (0.34 µM) was then added and the rate of Factor Xa formation determined.

In order to determine which region of Factor VII mediated the binding to tissue factor, the synthetic peptides were utilized to inhibit the binding of Factor VII to the tissue factor expressing bladder carcinoma cell line, J82. Varying amounts of synthetic peptide were mixed with the cells for 30 minutes at 37 degrees Centigrade, after which Factor VII was added for 15 minutes. The cells were washed, Factor X was added to the cells, and the rate of Factor Xa formation was determined. Of the peptides tested, only the peptide 206-218 inhibited the rate of Factor Xa formation in a dose-dependent manner (FIG. 9). Higher concentrations of the synthetic peptides were required probably because of the high affinity of the Factor VII-tissue factor interaction as previously described (2). Because the affinity of the synthetic peptide for tissue factor is low relative to Factor VII, and because Factor VII binds to phospholipid in the presence of calcium ion which increases its relative concentration at the cell surface, higher concentrations of synthetic peptide were required to prevent the association of Factor VII with tissue factor.

Figure 10:
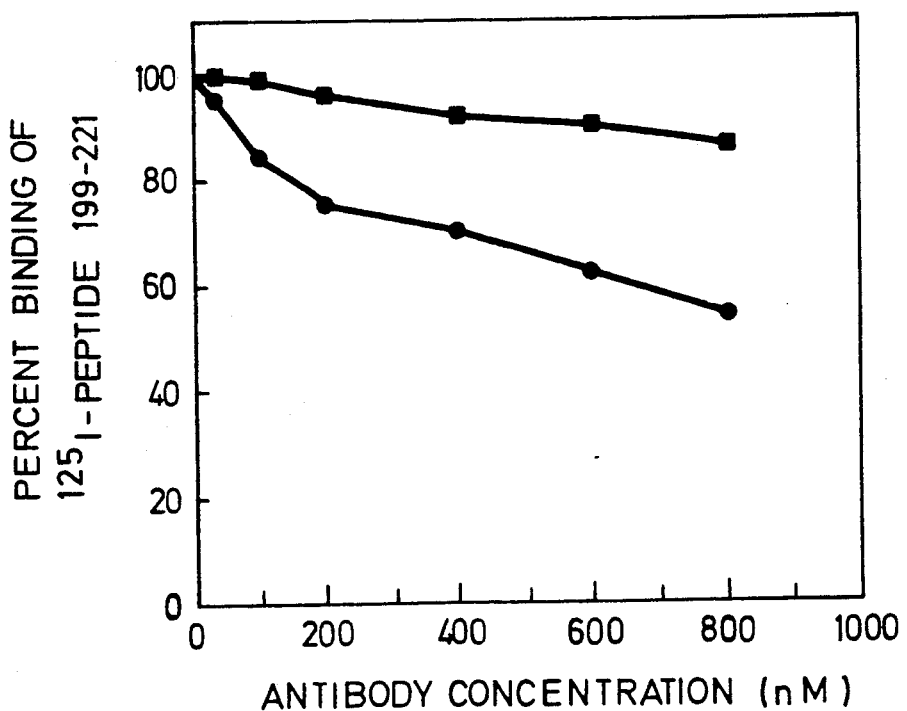
FIG. 10. Inhibition of the binding of $^{125}$I-peptide 199–221 to J82 cells by a monoclonal antibody to tissue factor. Confluent cultures of J82 were incubated with varying concentrations of either normal mouse IgG (square) or monoclonal antibody (circle) for 60 min at 37 degrees Centigrade. Radioiodinated peptide 199–221 was added to the mixture for 30 min at room temperature, the peptide was crosslinked using Bis(sulfosuccinimidyl) suberate, and the cells washed, lysed and counted in a gamma counter. The data are presented as binding of peptide versus antibody concentration.

The ability of a monoclonal antibody to human tissue factor to prevent the binding of selected peptides to J82 cells was also tested. Radiolabeled peptide 199-221 (a tyrosine was substituted for a tryptophan at amino acid position 201 for labeling) was shown to bind to the cells in a saturable manner (data not shown). Competitive inhibition assays demonstrated that the monoclonal antibody to human tissue factor relative to nonimmune mouse IgG could prevent the binding of the peptide to the J82 cells (FIG. 10). Presumably the monoclonal antibody binds to tissue factor. The monoclonal antibody did not completely block peptide association with the cells, a finding that can be explained as resulting from background or non-specific interactions between the peptide and the cell surface, an interpretation supported by the ability of unlabeled peptide to completely inhibit binding of labeled peptide (data not shown).

The data above, coupled with the data obtained from the kinetic assay suggest that the sequence 208-218 represented in the peptide 199-221 mediates the association of this protein with tissue factor.

Because of the mutual non-exclusivity observed between peptide 209-221 and peptide 285-305, the peptide 285-305 may represent a site on Factor VII distal from the region represented by peptide 208-229. If peptide 208-229 represents the tissue factor interacting site, then peptide 285-305 may represent the substrate recognition site on Factor VII.

USE OF THE PEPTIDES TO INHIBIT COAGULATION IN VIVO

Due to precautions necessarily attendant to development of every new pharmaceutical, the coagulation inhibitory peptides of the present invention have not yet been tested in a clinical setting in human subjects. Therefore, the in vitro activity of the peptides has been used to demonstrate the utility of the present invention; these assays are accepted by those of skill-in-the-art as reliable indicators of in vivo activity. The following prophetic embodiments represent the preferred mode presently contemplated by the present investigators for carrying out the practice of the invention in various clinical settings.

First, it is believed that the antihemostatic peptides will prove to be useful in treating numerous diseases in which thrombotic disorders are involved. In particular, these include, but are not limited to deep vein thrombosis, pulmonary embolism, arterial thrombotic diseases including acute arterial occlusion and disseminated intravascular coagulation.

For treatment, the coagulation inhibitory peptides may be formulated into pharmaceutical compositions and administered using a therapeutic regimen compatible with the particular formulation. As described further below, with the aid of the present disclosure, those of skill in the pharmaceutical and medical arts should be able to derive suitable dosages and schedules of administration for any of a number of effective compositions containing the anticoagulant peptides. Accordingly, pharmaceutical compositions within the scope of the invention include compositions where the active ingredient is contained in an effective amount to achieve its desired anticoagulant activity. However, a preferred dosage comprises that which is sufficient to achieve an effective blood concentration of about 3 to 50 micromolar of peptide which is equal to 5 to 75 μg/ml. Assuming 6 liters of blood in an average person, the total dosage would be to 30 to 450 mg of peptide or for a 150 kg human (0.2 to 3. mg/kg). Nevertheless, although a preferred range has been described, determination of the effective amounts for treatment of any particular patient or thrombotic disorder(s) should be determined by those of skill-in-the-art.

Although the most efficacious manner of administering the anticoagulant peptide will depend on the particular clinical situation, it is believed that in many cases the peptides may be most easily administered by formulating such with a suitable pharmaceutical excipient or the vehicle in administering the formulation intravenously. Alternatively, the peptides may be formulated for intramuscular, subcutaneous, intradermal, or intra-articular injections; such injections might be used to treat pathologic conditions at the sites when thrombosis is involved.

In addition to the anticoagulant compounds, the pharmaceutical compositions may contain any of a number of suitable excipients and auxiliaries that facilitate process of the active compounds into preparations that can be used pharmaceutically. As indicated above, although the preparations will most commonly be designated for parenteral administration, compositions designed for oral or rectal administration are also considered to fall within the scope of the invention. Generally, preferred compositions will comprise from about 0.05% to 5.0% by weight of active ingredients. Suitable formulations for parenteral administration include aqueous solutions of the active compounds in water-soluble or water dispersible form. In addition, in some cases, suspensions of the active compounds may be administered in suitable lipophilic carriers. The formulations may contain substances that increase viscosity, for example, sodium carboxymethyl cellulose, sorbitol and/or dextran. Optionally, the formulation may also contain stabilizers.

With each formulation, suitable excipients, for example, saline, lipids or physiologic buffers, are known to those of skill-in-the-art and may be used.

The foregoing description of the invention has been directed to particular preferred embodiments in accordance with the requirements of the patent statues and for purposes of explanation and illustration. It will be apparent, however, to those skilled in the art that many modifications and changes may be made without departing from the scope and the spirit of the invention.

For example, the peptides may be modified from those disclosed herein in a number of particulars that do not significantly affect the anticoagulant activity. Such particulars may include, but are not limited to, conservative amino acid substitutions and modifications, including, for example, amidation of the carboxyl terminus, acetylation of the amino terminus, conjugation of the polypeptide to a physiologically inert carrier molecule, or other sequence alterations, such as dilution or addition of a limited number of amino acids, so long as such changes do not significantly affect the peptides anticoagulant properties. It is apparent that the invention may also be utilized with other suitable modifications within the state-of-the-art. It is the applicants intention in the following claims to cover all such equivalent modification and variations which fall within the true spirit and scope of the invention.

REFERENCES

Colman, R. W., Marder, V. J., Salzman, E. W., and Hirsh, J. (1987) in Hemostasis and Thrombosis. Basic Principles and Clinical Practice, 2nd edition (Colman, R. W., Marder, V. J., Salzman, E. W. and Hirsh, J., ed.) J. B. Lippincott Company, pp 3-17.

2. Nemerson, Y. (1988) Blood 71:1-8.

3. Weiss, H. J. and Lages, B. (1988) Blood 71:629-635.
4. Weiss, H. J., Turitto, V. T., Baumgartner, H. R., Nemerson, Y. and Hoffman, T. (1989) Blood 73:968-975.
5. McLacklin, A. D. (1971) J. Mol. Biol. 61:409-424.
6. Fair, D. S. (1983) Blood 62:784-791.
7. Fair, D. S., Plow, E. F., and Edgington, T. S. (1979) J. Clin. Invest. 64:884-894.
8. Burri, B. J., Edgington, T. S. and Fair, D. S. (1987) Biochim. Biophys. Acta 923:176-186.
9. Morrissey, J. H., Revak, D., Tejada, P., Fair, D. S. and Edgington, T. S. (1988) Thromb. Res 50:481-493.
10. Hagen, F. S., Gray, C. L., O'Hara, P., Grant, F. J., Saari, G. C., Woodbury, R. G., Hart, C. E., Insley, M., Kisiel, W., Kurachi, K. and Davie, E. W. (1986) Proc. Natl. Acad. Sci. USA 83:2412-2416.
11. Glass, J. D. B. (1983) Meth. Enzymol. 99:119-139.
12. Segel, I. R. (1975) *Enzyme Kinetics: Behavior* and *Analysis of Rapid Equilibrium and Steady-State Enzyme Systems,* John Wiley & Sons, New York, pp. 465-504.
13. Chattopadhyay, A. and Fair, D. S. (1989) J. Biol. Chem. 264:11035-11043.
14. Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D. C. (1985) Anal. Biochem. 150:76-85.
15. March, S. C., Parikh, I. and Cuatrecasas, P. (1974) Anal. Biochem. 60:149-152.
16. Fair, D. S. and MacDonald, M. J. (1987) J. Biol. Chem. 262:11692-11698.
17. Morrissey, J. H., Fair, D. S. and Edgington, T. S. (1988) Thromb. Res. 52:247-261.
18. Fraker, P. J. and Speck, J. C. (1978) Biophys. Res. Commun. 80:849-857.

What is claimed is:

1. A pharmaceutical formulation for the treatment of clotting disorders comprising a peptide consisting essentially of from about 10 to about 36 amino acids in length characterized in that said peptide inhibits the rate of extrinsic pathway mediated activation of Factor X by at least about 40%, and said peptide includes an amino acid sequence that is at least 90% homologous to the sequence G-E-H-D-L-S-E-H-D-$\bar{\text{G}}$, together with a pharmaceutically acceptable excipient.

2. A pharmaceutical formulation for the treatment of clotting disorders comprising a peptide consisting essentially of from about 10 to about 36 amino acids in length characterized in that said peptide inhibits the rate of extrinsic pathway mediated formation of the Factor VII-tissue factor complex by at least about 40%, and said peptide includes an amino acid sequence that is at least 90% homologous to the sequence G-E-H-D-L-S-E-H-D-G, together with a pharmaceutically acceptable excipient.

3. A pharmaceutical formulation for the treatment of clotting disorders comprising a peptide consisting essentially of from about 10 to about 36 amino acids in length characterized in that said peptide inhibits the rate of thrombin formation by at least about 40%, and said peptide includes an amino acid sequence that is at least 90% homologous to the sequence G-E-H-D-L-S-E-H-D-G, together with a pharmaceutically acceptable excipient.

4. The pharmaceutical formulation according to claims 1, 2, or 3 wherein said peptide includes a stretch of amino acids having the sequence L-G-E-H-D-L-S-E-H-D-G.

5. The pharmaceutical formulation according to claims 1, 2, or 3 wherein said peptide includes a stretch of amino acids having the sequence L-G-E-H-D-L-S-E-H-D-G-D-E-Q-S-R-R-V-A-Q-V-I-G-C.

6. The pharmaceutical formulation according to claims 1,2, or 3 wherein said peptide includes a stretch of amino acids having the sequence C-F-D-K-I-K-N-W-R-N-L-I-A-V-L-G-E-H-D-L-S-E-H-D-G-D-E-Q-S-R-R-V-A-Q-V-I.

7. The pharmaceutical formulation according to claims 1,2, or 3 wherein said peptide includes a stretch of amino acids having the sequence F-D-K-I-K-N-W-R-N-L-I-A-V-L-G-E-H-D-L-S-E-H-D-G-D-E-Q-S-R-R-V-A-Q-V-I.

8. A substantially purified preparation of immunoglobulin having immunologic specificity for a peptide of any one of claims 1, 2, 3, 4, 5, 6, or 7.

* * * * *